United States Patent [19]

Stavrianopoulos

[11] Patent Number: 5,013,831
[45] Date of Patent: May 7, 1991

[54] DETECTABLE MOLECULES, METHOD OF PREPARATION AND USE

[75] Inventor: Jannis G. Stavrianopoulos, New York, N.Y.

[73] Assignee: Enzo Biochem, Inc., New York, N.Y.

[21] Appl. No.: 521,762

[22] Filed: May 8, 1990

Related U.S. Application Data

[60] Continuation of Ser. No. 43,668, Apr. 28, 1987, Pat. No. 4,952,685, which is a division of Ser. No. 575,396, Jan. 30, 1984, Pat. No. 4,707,440.

[51] Int. Cl.$^5$ .............................................. C07H 15/12
[52] U.S. Cl. .......................................... 536/27; 435/6; 536/28; 536/29
[58] Field of Search ...................... 536/27–29; 435/6

[56] References Cited

U.S. PATENT DOCUMENTS 4,828,979  5/1989  Klevan et al. ............... 536/27 X
4,843,122  6/1989  Stavrianopoulos ........... 536/27 X
4,876,335  10/1989  Yamane et al. .............. 536/27

Primary Examiner—Christine Nucker
Attorney, Agent, or Firm—Serle I. Mosoff; Elaine P. Brenner

[57] ABSTRACT

A detectable molecule of the formula

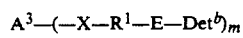

where $A^3$ is $A^2$ or a polymer, where $A^3$ has at least one modifiable reactive group selected from the group consisting of amino, hydroxy, cis OH, halides, aryl, imidazoyl, carbonyl, carboxy, thiol or a residue comprising an activated carbon; —X— is selected from the group consisting of

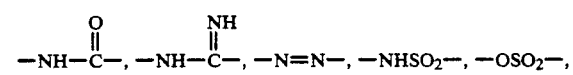

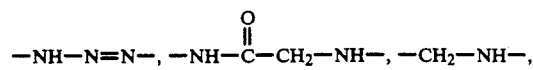

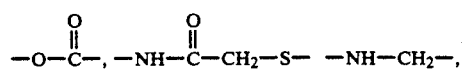

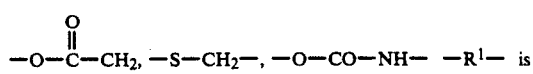

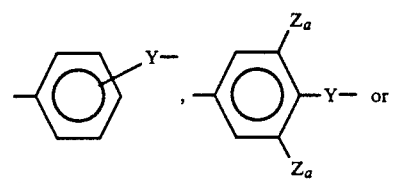

a $C_1$-$C_{10}$ branched or unbranched alkyl or aralkyl, which may be substituted by —OH; —Y— is a direct bond to —E—, or —Y— is —E—$R^2$— where $R^2$ is a $C_1$-$C_{10}$ branched or unbranched alkyl; $Z_a$ is chlorine, bromine or iodine; E is O, NH or an acyclic divalent sulfur atom; Det$^b$ is a chemical moiety capable of being detected, preferably comprising biotin or a metal chelator of the formula:

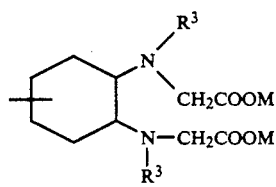

or the 4-hydroxy or acyloxy derivative thereof, where $R^3$ is $C_1$-$C_4$ alkyl or CH$_2$COOM, M is the same or different and selected from the group consisting of hydrogen, a metal or non-metal cation or is $C_1$-$C_{10}$ alkyl, aryl or aralkyl; and m is an integer from 1 to the total number of modified reactive groups on $A^3$. The detectable molecules are useful in in vitro or in vivo assays or therapy.

2 Claims, No Drawings

DETECTABLE MOLECULES, METHOD OF PREPARATION AND USE

This is a continuation of application Ser. No. 043,668 filed Apr. 28, 1987 now U.S. Pat. No. 4,952,685, which is a division of application Ser. No. 575,396 filed Jan. 30, 1984, now U.S. Pat. No. 4,707,440.

BACKGROUND OF THE INVENTION

1. Field of the Invention

The present invention relates to the preparation and use of molecules carrying attached thereon metal complexing agents or biotin-containing detectable groups, as well as the products themselves.

2. Description of the Prior Art

The use of radioactively labelled diagnostic and therapeutic agents obtained by labeling such agents with metal ions has recently received renewed interest. In this technique, a chelating moiety is covalently attached to the molecule of interest, and a radioactive ion is chelated by the sequestering groups of the chelator. The radioactively labelled agents can then be used both in vitro (for example in radioimmunoassay systems) and in vivo (for example, both in diagnostic imaging techniques and in radiation therapy techniques). The use of metal labelling of the nonradioactive type is also of interest, as for example, in the utilization of nuclear magnetic resonance, electron spin resonance, catalytic techniques, and the like.

Different metal chelating groups have been attached to biopolymers in the prior art. Activated analogues of ethylenediaminetetraacetic acid (EDTA) derived from 1-(p-benzenediazonium)EDTA (I) have been used on proteins:

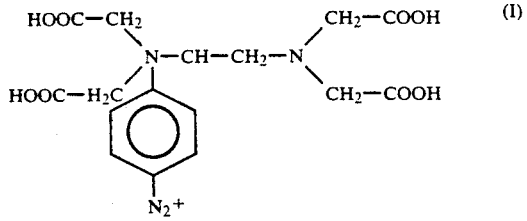

(See, for example, Meares et al. U.S. Pat. No. 4,043,998, Sundberg et al. Journal of Medicinal Chemistry 17:1304–1307 (1974); or Sundberg et al., Nature 50:587–588 (1974).) The p-benzenediazonium EDTA of formula I is coupled via an azo linkage to selected tyrosine, histidine or amine residues of proteins, the latter forming triazines which are acid labile.

Diethylenetriaminepentaacetic acid (DTPA) is a metal chelator which has also been attached to polypeptides (see, for example, Krejcarek et al Biochemical Biophysical Research Communications 77:582–585 (1977), Hnatovich Science 220: 613–615 (1983), or Khaw, ibid, 209:295–297 (1980).) The chelator is attached through one of its carboxyl groups via an amide linkage to a protein-derived amino group, as shown in formula II:

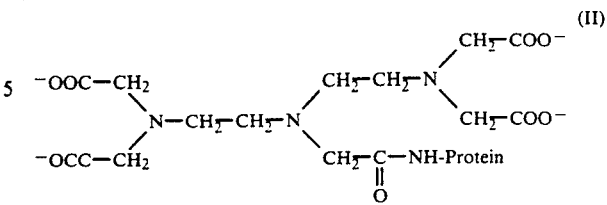

This DTPA conjugate is achieved by first preparing the di-anhydride and reacting the same with a protein. (See for example, Scheinberg, Science 215:1511–1513 (1982).) Involvement of the di-anhydride, however, may cause potential crosslinking problems which are either intramolecular or intermolecular. Also, attachment of the chelator through one of its carboxy groups may remove this carboxy group from consideration as a complexing moiety, thus decreasing the chelating efficiency, by a modification of the binding affinity constant and geometry.

Wieder et al U.S. Pat. No. 4,352,751 also suggest the attachement of metal chelating groups to proteins, utilizing trans-diaminocyclohexanetetraaacetic acid (DCTA), attached through one of its carboxy groups to the amino group of a protein. As a model, Wieder et al show the reaction with ethylamine to form compound (III):

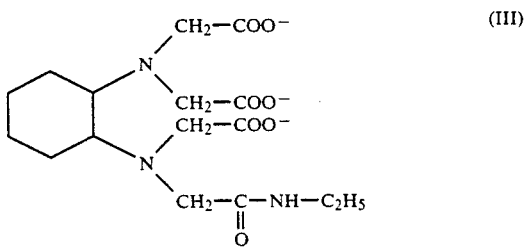

This compound may suffer from the same problems as the DTPA complex, in that conjugation occurs through one of the carboxy groups, thus potentially decreasing the binding affinity, and modifying the geometry of the resulting metal complexes.

Other metal chelating groups have also been attached to biopolymers, e.g., methylpicolinimidate on lysozyme (Benisek et al, J. Biol. Chem., 243:4267–4271 (1968)), ferritin on monoclonal antibodies (Block et al, Nature 301:342–344 (1983)), and the like. A possible means of overcoming the aforementioned problems of loss of affinity, limitation on protein reactive residues, and change in geometry or crosslinking is disclosed in commonly assigned copending patent application Ser. No. 391,440 filed on June 23, 1982 for "Modified Nucleotides, Methods of Preparing and Utilizing, and Compositions Containing the Same" by Engelhardt et al, which is herein fully incorporated by reference. The Engelhardt et al application discloses the coupling of a thiocyanate derivative of DCTA to an allylamine-modified deoxyUTP and its possible incorporation into polynucleotides. See IV:

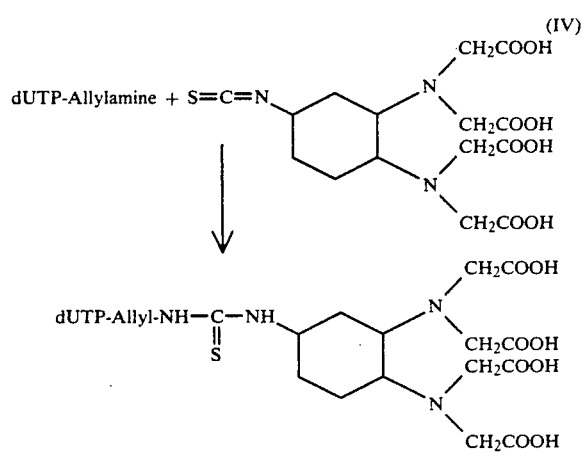

The use of the deoxyUTP allylamine and its attachment to other detectable groups, such as biotin, has also been disclosed (See, for example Langer et al Proc. Nat. Acad. Sci. 78:6633–06637 (1981)) or copending U.S. application Ser. No. 255,223 filed Apr. 17, 1981 at the U.S. Patent and Trademark Office to Ward et al, entitled "Modified Nucleotides and Methods of Preparing and Using Same," herein incorporated by reference).

There would be an advantage to utilize the DCTA chelating agent or other chelating agents without having to extensively modify nucleotides a priori, to utilize physiological chemical process conditions, and to provide a wide range of alternative methods utilizable in polypeptide, polynucleotide, polysaccharide and small molecular chemistry.

The development of such methodology would allow the use of high affinity, versatile metal chelating agents such as DCTA, and might also be extended and applied to the attachment of other chelators or detectable moieities, such as biotin.

SUMMARY OF THE INVENTION

The present invention is partly based on the discovery of methods of the quick, mild and versatile attachment of metal chelating groups and biotin to polymers, and especially biopolymers such as polynucleotides, polypeptides or polysaccharides. The attachment methods include both the use of known intermediate linking agents (which, however, had heretofore not been used for this purpose), or in some instances, includes the development of novel linking or bridging groups. The invention also relates to the products obtained from these methods and extends to products comprising both polymers linked to chelators and analogues thereof, to biotin and analogues thereof, and to various intermediates.

In addition, the invention also provides certain low molecular weight (MW less than about 2,000) molecules linked to a variety of detectable agents such as various chelating agents, and also to biotin moieties. The low molecular weight compounds can be linked by direct bonds or by any known linking arms to any chelating molecule or potentially chelating molecule. The low molecular weight conjugates between low molecular weight compounds and chelating molecules thus have the formula (V):

$$A^1 \cdots Det^a \quad (V)$$

where $A^1$ is a low molecular weight compound of molecular weight preferably below 2,000, and $Det^a$ is biotin or a detectable chemical moiety comprising a substituted or unsubstituted metal chelator or a compound capable of yielding a metal chelating compound, most preferably one of the formula (VI):

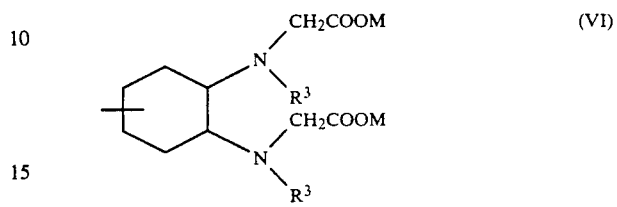

where M and $R^3$ are defined below; and the link "⋯" indicates a direct covalent bond or an appropriate spacer arm which does not interfere with the signalling ability of $Det^a$, with the molecular recognition properties of $A^1$ and which assures a stable conjugate between $A^1$ and $Det^a$.

In a preferred embodiment, another aspect of the invention comprises a detectable molecule of the formula (VII):

$$A^3(X-R^1-E-Det^b) \quad (VII)$$

where $A^3$ is $A^2$ or a polymer, both $A^2$ or the polymer having at least one modifiable reactive group selected from the group consisting of amino, hydroxy, cis 1,2-di OH, halide, aryl, imidazoyl, carbonyl, carboxy, thiol or a residue comprising an activated carbon;

$A^2$ is a chemical entity having a molecular weight of less than about 2,000;

—X— is selected from the group consisting of —NH—CO—, —NH—CNH—, —N═N—, —NH—SO₂—, —OSO₂—, —NH—N═N—, —NH—CH₂—, —CH₂—NH—, —O—CO—, —NH—CO—CH₂—S—, —NH—CO—CH₂—NH—, —O—CO—CH₂—, —S—CH₂—; —O—CO—NH—

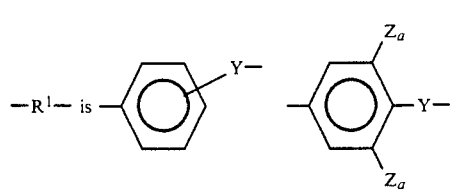

or a $C_1$-$C_{10}$ branched or unbranched alkyl or aralkyl, which may be substituted by OH;

—Y— is a direct bond to —S—, or —Y— is —S—$R^2$—, where $R^2$ is a $C_1$-$C_{10}$ branched or unbranched alkyl;

$Z_a$ is chlorine, bromine or iodine;

E is O, —N— or an acyclic divalent sulfur atom;

$Det^b$ is a detectable chemical moiety comprising biotin or a substituted or unsubstituted metal chelator, or a compound capable of yielding a metal chelating compound, preferably a compound of the formula:

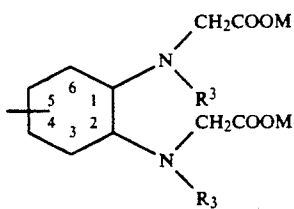

where $R^3$ is $C_1$–$C_4$ alkyl or is —$CH_2$—COOM, and each M is a suitable cation;

m is an integer from one to the total number of modified reactive groups on $A^3$.

Yet another aspect of the present invention comprises a detectable modecule of the formula:

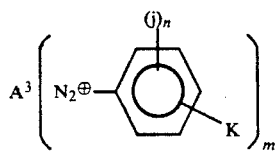

wherein $A^3$ is as defined above, j is an electron withdrawing group, K is a signal generating entity or a solid matrix, r is an integer from one to about two and n is as defined above.

Other specific aspects of the invention comprise individual nucleotides, saccharides or amino acids modified with a group X—$R^1$—E—Det as above. Still other aspects of the invention relate to synthetic methods of preparing, as well as general methods of using the aforementioned products.

The resulting covalent conjugates between the biopolymers or small molecules and metal chelators or biotin moieties are utilizable in a wide range of applications. For example, the products can be used as detectable products, by chelating radiometals thereto. They can then be used in a wide range of in vivo and in vitro therapeutic, diagnostic, imaging and assay (immunoassay or hybridization assay) techniques. Biotin labelled biopolymers or small molecules can be used as detectable molecules wherever biotin/avidin or biotin/streptavidin-based pairs or detection systems have been used in the prior art. The synthetic polymers of the invention can be utilized in the same applications as the biopolymers or small molecules, by attaching the synthetic polymer to biopolymers or small molecules. Thus, for example, such synthetic polymers can provide numerous radiometals per biopolymer or small molecule, which results in a very strong signal being produced.

The ease on introduction, physiological process conditions, versatility and other such advantages using the DCTA-based chelating agents are particularly capable of providing a chelator with high affinity, without loss of its geometry, and avoidance of crosslinking in its introduction. The methods also have the ability of introducing, at least with certain linking procedures described hereinbelow, quantitatively more labeling agent per molecule than the prior art.

BRIEF DESCRIPTION OF THE PREFERRED EMBODIMENTS

Products

By the small molecular weight entity $A^2$ is meant to include the so called ligands generally involved in immunoassays for their determination. These include drugs which are used for therapeutic purposes, naturally occurring physiological compounds, metabolites, pesticides, pollutants, enzyme substrates, the reaction product of an enzyme and its substrate, and the like. (For a list of useful entities $A^2$ see, for example columns 12, 13, 14 and 15 of Rowley et al. U.S. Pat. No. 4,220,722, herein fully incorporated by reference.) For example, included in $A^2$ are alkaloids, steroids, lactams, aminoalkylbenzenes, benzheterocyclics, purines, vitamins, prostaglandins, antibiotics, amino acids, pesticides, and the like. The molecular weight of $A^2$ is less than about 2,000, especially less than about 1,000.

By the small molecular weight compound $A^1$, on the other hand are included all of the aforementioned compounds for $A^2$ with the proviso that $A^1$ is not a monosaccharide, or a mononucleotide. Preferably $A^1$ is not an amino acid either. $A^1$ thus generally comprises such compounds as pesticides, drugs, pollutants, other physiological compounds, and the like. For example $A^1$ includes alkaloids, steroids, lactams, aminoalkylbenzenes, benzheterocyclics, prostaglandins, antibiotics and the like.

Certain other products within the present invention are detectable polymers which comprise synthetic polymers and biopolymers such as polynucleotides, polypeptides or polysaccharides, or larger fractions containing these.

By "polynucleotide" is meant to include both polyribonucleotides, polydeoxyribonucleotides, or anypolypurine, poly-pyrimidine or analogue, or combinations thereof. Examples are DNA, RNA, or fragments thereof.

By "polypeptide" is meant to include any polyamino acid chains, whether high or low in molecular weight. These include proteins, hormones, enzymes, immunoglobulins, such as for example, monoclonal antibodies, protein complexes, and the like.

By "polysaccharide" is meant to include any polysaccharide either naturally or non-naturally occurring, linear, non-linear or crosslinked, aqueous-soluble or insoluble, unsubstituted or partly or wholly substituted. These include cellulose, starch, amylose, amylopectin, and the like.

By "synthetic" polymer is meant to include any synthetic polymer having at least one modifiable reactive group selected from the group consisting of amino, hydroxy, 1,2- cis di OH, halides, aryl, imidazoyl, carbonyl, carboxy, thiol or a residue comprising an activated carbon. Nonlimiting examples of suitable polymers that can be modified to have such a modifiable reactive group include polyethylene, polyacrylamide, polyurethane, polystyrene, polyethylene glycol, polybutadiene, polyvinyl alcohols and halides and copolymers thereof. If the polymer does not contain the modifiable reactive group, then such group can be attached to the polymers by any of the methods well known to those having ordinary skill in the art of organic chemistry.

It is necessary that the entity $A^3$ (which can be either $A^2$, supra, or a polymer) prior to reaction have at least one and up to several modifiable reactive groups selected from the group consisting of amino groups (such as for example -amino group of lysine, amino groups in proteins, amino groups in aminopolysaccharides or reactive amino groups on nucleotide bases), hydroxy groups or cis OH groups (such as for example those in steroids, saccharides, serine or in sugar moieties of polynucleotides, such as terminal 3' or 5' hydroxy), carboxyl groups (such as for example aspartate, glutamate, or derivatives thereof), thiol groups (such as for example cysteine), carbonyl groups (such as those existing in certain steroids, alkaloids, on terminal portions of naturally occurring proteins, or obtainable by modification, as is shown hereinbelow), or residues comprising activated carbon groups (such as the C-3 or C-5 carbon site on tyrosine residues, the C-4 site in histidine residues, the reactive carbon site on guanine, inosine, cytidine or analogues thereof. For example, guanine has a reactive carbon atom at position C-8.) Also, $A^3$ can have modifiable reactive groups such as imidazoyl groups in proteins as part of a histidine residue or aryl groups as part of tyrosine residue, or halides as part of a synthetic polymer. The reactive carbon atoms of these molecules or molecular portions of $A^3$, should be capable of covalently reacting with electrophiles such as diazoaryl functionalities, and undergo coupling (e.g., diazo coupling reactions).

The modifiable reactive group on $A^3$ may also be present by modification of $A^3$, and introduction thereinto of such a group. It may also be present, for example, in an enzyme cofactor which may be linked, covalently or noncovalently with a polypeptide.

The number of modifiable reactive groups on $A^3$ will depend on the presence or absence of such groups in $A^2$ or certain reactive amino acids, bases or saccharides in the polypeptide, polynucleotide or polysaccharide, respectively. This, in the case of the biopolymer, will depend on the actual chemical composition of the biopolymer, on the molecular weight thereof, as well as the three dimensional structure of the biopolymer, and thus the relative accessibility of reactive groups to the approach and covalent interaction with reactive partners. It is known, for example, that in proteins there are certain residues which are more reactive than others, given the fact that they may be closer to the surface, present in certain active regions, or the like. When the biopolymer is modified according to the present invention, with an excess of modifying reagent, the aforementioned factors will determine the amount and extent of modification. Thus, one, several and possibly all reactive residues, bases or sugar moieties may react with an appropriate reactive partner.

Alternatively, an individual unit of a biopolymer, such as an individual amino acid or an individual nucleotide or saccharide might be previously modified, and then incorporated into a final, build-up biopolymer.

In any event, it is a matter of routine to those of ordinary skill in the art to estimate whether there exist reactive residues in a given entity $A^2$ or biopolymer, and how many such residues have reacted, in order to determine the final stoichiometry of the conjugate between $A^2$ or the biopolymer and the modifying group. Such techniques as radiolabeling can be used to estimate the extent of modification, and to actually count the number of modified reactive groups. In most instances, the number of actually modified groups will be less than the number of potentially available modifiable groups of any particular chemical species.

Among the preferred products of the invention are those of the formula (VII):

$$A^3\text{—}(X\text{—}R^1\text{—}S\text{—}Det^b) \qquad (VII)$$

where $A^3$ is $A^2$ or the biopolymer comprising a polynucleotide, polypeptide or polysaccharide.

—X— generally comprises a covalent bonding function between one of the $A^3$-modifiable reactive groups and the group $R^1$. X may be a single function, such as an amide or ester, or —X— may be a bridge or link between a modifiable reactive group on $A^3$ and the $R^1$ group. For example, when X is —NH—CO—, the —NH portion thereof is normally derived from an amine functionality of $A^1$ or of the biopolymer, and X is a standard amide group. When X is —N=N— (azo linkage), this linkage is usually attached to an activated carbon-containing modifiable group on $A^2$ or on the biopolymer.

$R^1$ may be unsubstituted phenyl or phenyl substituted by a halogen such as chlorine or bromine. $R^1$ may also be a phenyl substituted by a group —Y— where Y may be a direct covalent bond to —S— or may be —S—$R^2$—. $R^2$ may be divalent $C_1$-$C_{10}$ branched or unbranched alkyl, preferably lower alkyl ($C_1$-$C_6$), most preferably methyl, ethyl, propyl, isopropyl, n-butyl, isobutyl or pentyl.

$R^1$ may also be a divalent $C_1$-$C_{10}$ branched or unbranched alkyl, as described for $R^2$, supra, and preferably lower alkyl ($C_1$-$C_6$), most preferably $C_2$-$C_4$. $R^1$ may also be a $C_1$-$C_{10}$ aralkyl, such as phenyl substituted by lower alkyl, especially benzyl.

$Det^b$ is a detectable chemical moiety which comprises either biotin, or a modified biotin molecule, or comprises $Det^a$, which is a metal chelating compound or a compound capable of yielding a metal chelating compound. Preferred among these compounds are such molecules as EDTA, DTPA or DCTA or analogues or homologues thereof. Most preferred is the compound of the formula (VIII):

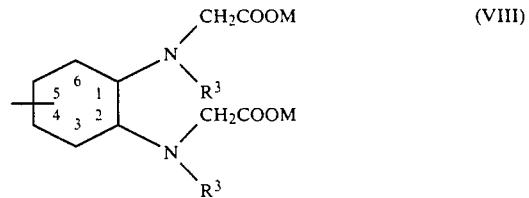

(VIII)

This formula depicts a cyclohexane-based metal chelator which may be attached to sulfur S through positions 4 or 5, and which carries from 1 to 4 metal or nonmetal cations, monovalent cations or the alkaline earth metals. Thus, with metals of oxidation state +1, each individual cyclohexane-based molecule may carry up to 4 metal cations (where both $R^3$ groups are $CH_2COOM$). As is more likely, with higher oxidation states, the number of metals will decrease to 2 or even 1 per cyclohexane skeleton. The cyclohexane functionality admits of varying stereochemistry, and the aforementioned formula is not intended to limit the molecule to any specific stereochemistry. In particular, both amino functionalities may be either cis or trans to each other.

The cyclohexane may be unsubstituted (except for the two nitrogen functionalities and the sulfur substituent) or may be substituted, especially at the 4-position, with a hydroxy or acylated hydroxy group, such as with a lower acyl substitution.

For purposes of this invention, other cyclohexanebased analogues such as alkyl derivatives (e.g., lower alkyl) or substitution products, wherein the derivatization or substitution do not interfere with the linking of the cyclohexane skeleton to sulfur, with the chelating ability (affinity, geometry, etc.) of the individual chelating moieties, or with the overall biological activity of the modified $A^3$ are equivalent to those actually shown. Substitutions which are equivalent for the purposes of this invention are such as hydroxy, acyl, halogen, amino, and the like.

The $A^3$ moieties having attached cyclohexane moieties may be in the acid form (M=H) or a non-radioactive metal or non-metal form (e.g., M=$Mg^{+2}$, Na' $K^+$, $Li^+$, $NH_4^+$, etc.) or in a radioactive metal form.

Any metal capable of being detected in a diagnostic procedure in vivo or in vitro, or capable of effecting therapeutic action in vivo or in vitro can be used. Both nonradioactive and radioactive metals can be utilized for this purpose. Thus, metals capable of catalyzing chemical reactions, metals capable of effecting NMR or ESR spectra, or metals capable of emitting radiation of various types or intensities could be utilized. Particularly, any radioactive metal ion capable of producing a therapeutic or diagnostic result in a human or animal body or in an in vitro diagnostic assay may be used in the practice of the present invention. Suitable ions include the following: Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-56, Cobalt-57, Cobalt-58, Cobalt-60, Erbium-169, Europium-152, Gadolinium-153, Gold-195, Gold-199, Hafnium-175, Hafnium-175+181, Indium 111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodynium-143, Promethium-147, Protactinium-233, Radium-226, Rhenium-186, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantallum-182, Tecnetium-99m, Tellurium-125, Tellurium-132, Turbium-160, Thallium-204, Thorium-228, Thorium-232, Thallium-170, Tin-113, Titanium-44, Tungsten-185, Vanadium-48, Vanadium-49, Ytterbium-169, Yttrium-88, Yttrium-90, Yttrium-91, Zinc-65, and Zirconium-95.

Preferred subgroups within the above formula (VII) are:

—NH—CO— combined with $C_1$-$C_{10}$ branched or unbranched alkyl;

activated carbon on tyrosine, histidine or guanine, inosine, or cytidine combined with —N=N—Aryl—, where aryl is as defined in formula (VII).

—NH—CO—$CH_2$—S— combined with $C_1$-$C_{10}$ branched or unbranched alkyl or with aryl, where aryl is as defined in formula (VII);

Specific examples of modified $A^3$ entities according to the present invention are shown in Table I below:

TABLE 1

| $A^2$ (modified reactive group) | X | R | S | Det |
|---|---|---|---|---|
| Dextran (OH) | —O—C—N— | —$CH_2$—$CH_2$— | S | DCTA |
| protein ($NH_2$) | —NH—C(=O)—$CH_2$—S— | —$CH_2$—$CH_2$— | S | DCTA |
| polynucleotide (G,$C^8$) | —N=N— |  | S | $CH_2CH_2NHCO(CH_2)_4$—Biotin |
| protein ($NH_2$) | —NH—C(=O)— | —$CH_2$—$CH_2$— | S | DCTA |
| protein (tyr, his) | —N=N— | 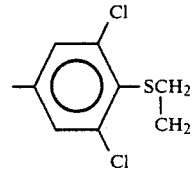 | S | DCTA |
| protein (tyr, his) | —N=N— |  | S | DCTA |
| polynucleotide (G,$C^8$) | —N=N— | 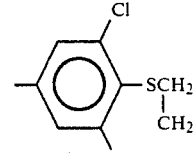 | S | DCTA |

TABLE 1-continued

| $A^2$ (modified reactive group) | X | R | S | Det |
|---|---|---|---|---|
| polynucleotide (uridineallyl amine) | $-NH-\overset{O}{\underset{\|}{C}}-$ | $-CH_2-CH_2-$ | S | DCTA |

Specific examples of $A^1$ or $A^2$ low molecular weight entities are digoxin, morphine, codein, heroin, diterpene alkaloids, estrogens, DES, barbiturates, amphetamines, catecholamines, chlorpromazine, azepines, diazepines, caffeine, theophylline, cannabinol, THC, penicillins, ethambuzol, chloromycetin, nitrofurantoin, methadone, serotonin, antihistamines, polyhalgenated biphenyls, phosphate esters, thiophosphates, carbamates, and metabolites, derivatives and analogues thereof.

Other preferred products of the invention are those of the formula (IX):

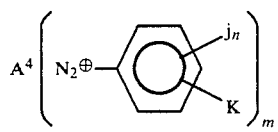

wherein a $A^4$ is $A^2$ or a polymer, both $A^2$ or the polymer having at least one modifiable reactive group selected from the group consisting of amino, aryl, imidazoyl and a residue comprising an activated carbon; $A^2$ is a chemical entity having a molecular weight less than about 2,000; j is an electron withdrawing group, K is a signal generating entity or a solid matrix, n is an integer from one to about two, preferably two, and m is as defined above.

j can be essentially any electron withdrawing group. Preferably, j is selected from the group consisting of chlorine, fluorine, bromine, sulfone groups and iodine, with chlorine being most preferred.

K can encompass virtually any of the signal generating entities used in the prior art, and any system to be developed in the future. It comprises a moiety which generates a signal itself, e.g. a radio label or a moiety which upon further reaction or manipulation will give rise to a signal, e.g. an enzyme linked system. Non limiting examples of suitable signal generating entities are disclosed in co-pending, co-assigned, U.S. patent application Ser. No. 391,440, filed on June 23, 1982. K can be attached to the benzene ring by any method known in the prior art. Also, K can be a solid matrix such as cellulose. The diazonium product can be fixed to cellulose by the method disclosed in Seed, U.S. Pat. No. 4,286,964.

The preferred products of formula (IX) are:

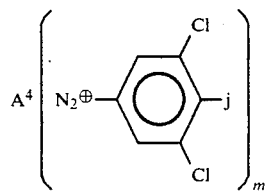

The products in formula IX are suprisingly stable and are strong electrophiles. Such stability and strong electrophilicity permits one to attach the products of formula (IX) to $A^3$ when the modifiable reactive group is very inert, such as the reactive carbon at the C-8 position of guanine. It is believed that such stability and strong electrophilicity is due to the electron withdrawing group or groups on the benzene ring.

Other products within the present invention are individual modified mononucleotides (ribo- and deoxyribo-) according to the formula (X):

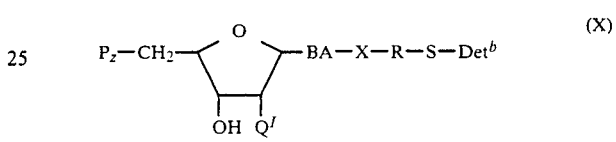

where $P_z$ is

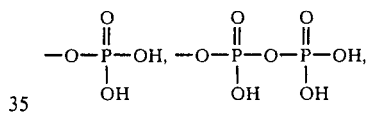

or metal or non-metal salts thereof;

$Q^1$ is H or OH;

BA is a modifiable purine or pyrimidine base, such as guanine, inosine, or cytidine.

Preferred among these products are those wherein BA has the formula (XI):

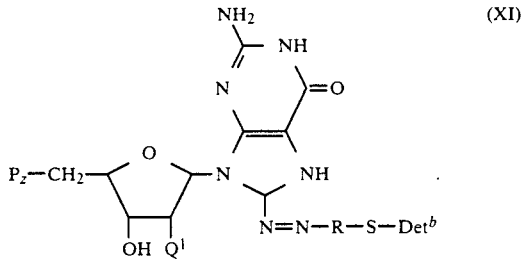

Still other products within the present invention are various intermediates which are described further hereinbelow.

Methods

Reactions involving the preferred cyclohexanebased skeleton can be carried out on DCTA or analogues, homologues, or substitution derivatives thereof, which are prepared according to any of the following Schemes:

Scheme I
Preparation of Bromo-DCTA

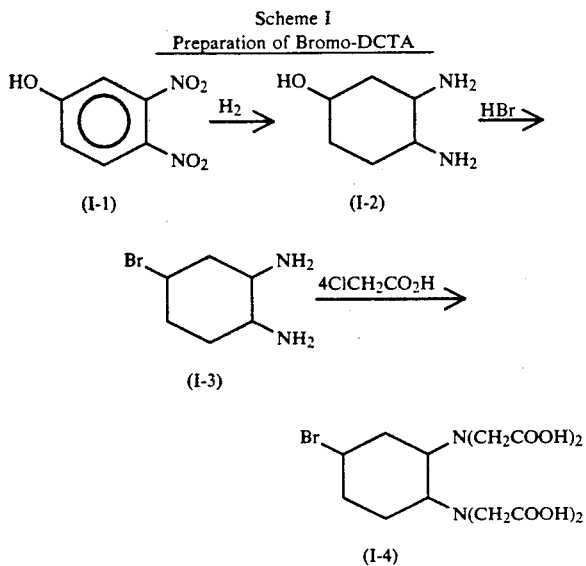

Scheme I shows the reduction of 3,4 dinitro phenol (I-1) to 3,4-diamino cyclohexane (I-2); bromination of 3,4-diaminocyclohexane to form 3,4-diaminobromocyclohexane (I-3); and further reaction of this compound with a halide-substituted carboxymethyl compound to produce the tetracarboxymethyl derivative thereof yielding the title compound (I-4). Details of these reactions can be found in Engelhardt et al, copending Ser. No. 391,440, filed June 23, 1982.

Scheme II
Preparation of Substituted DCTA
(exemplified by 4-hydroxy, 5-Bromo DCTA)

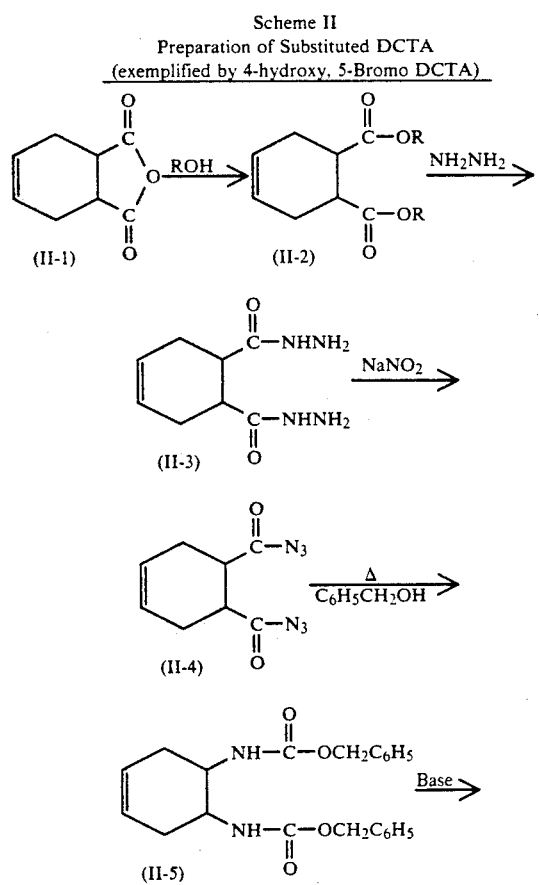

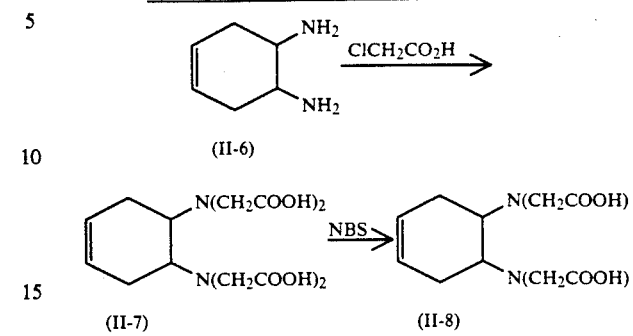

Scheme II shows the use of 4-cyclohexene-1,2-dicarboxylic anhydride (II-1) as a starting material. Reaction with alcohol followed by hydrazine yields a dihydrazide (II-3) which, when reacted with nitrate and heated, undergoes re-arrangement to a diurethane (II-5). Treatment of the diurethane with base leads to a diamine (II-6) which can than be carboxyalkylated to yield 1,2-diamino-4-cyclohexenetetraacetic acid (II-7). This compound can, for example, then be treated with N-bromosuccinimide (NBS) to yield 4-bromo-5-hydroxy DCTA derivative (II-8). Details of these reactions can be found in the accompanying Examples.

Scheme III
Preparation of Diamino
Cyclohexane N, N-(dialkyl, diacetic Acid) Derivatives

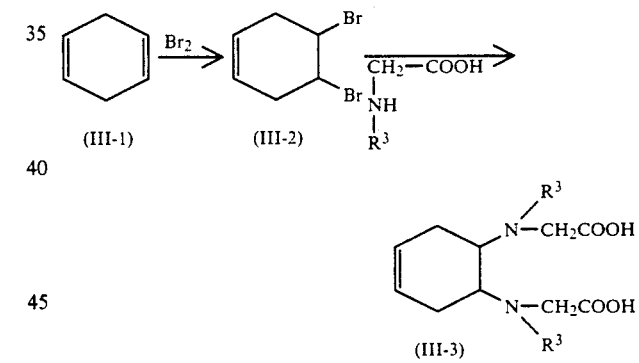

Scheme III shows the use of 1,4-cyclohexadiene (III-1) to produce dibromo derivative III-2, which can further be reacted with N-alkyl substituted glycine to yield the title compound (III-3).

In the above Schemes I, II or III, it is of course understood that different halogens, or even pseudohalogens could be used, since the object is to substitute the cyclohexane with a leaving group capable of being displaced by a mercapto group, SH. Such a leaving group could be chlorine, bromine, cyano, tosylate, mesylate, and the like.

The intermediates or starting materials used in these Schemes (such as for example the diester cyclohexene (II-2)), can be used for the preparation of further substituted cyclohexane skeletons as will be readily appreciated by one of skill in organic chemistry. Thus, a wide variety of modifications and substitutions can be introduced into the cyclohexane skeleton without affecting the basic chemistry of the chelating groups or of the displaceable leaving group.

The attachment of the (substituted or unsubstituted) cyclohexane skeleton to A³ is carried out via a basic nucleophilic substitution reaction between the oxygen, nitrogen or preferably, the sulfur atom of a thiol-containing compound, and the displaceable group or groups on the cyclohexane. The attachment can take any of three general routes.

First, one can attach the A³—X—R—SH moiety to the leaving group-containing cyclohexane by nucleophilic substitution.

Third, one can use a combination of both the first and second approaches, in that A³ is first reacted with part of the bridging group, which in turn is reacted with a previously modified cyclohexane to give the final conjugate.

In the second approach (Scheme IV, below), one can prepare a diazo aryl moiety-containing cyclohexane (IV-2, bonded to the cyclohexane via sulfur) and react the same with a protein or a polynucleotide as follows.

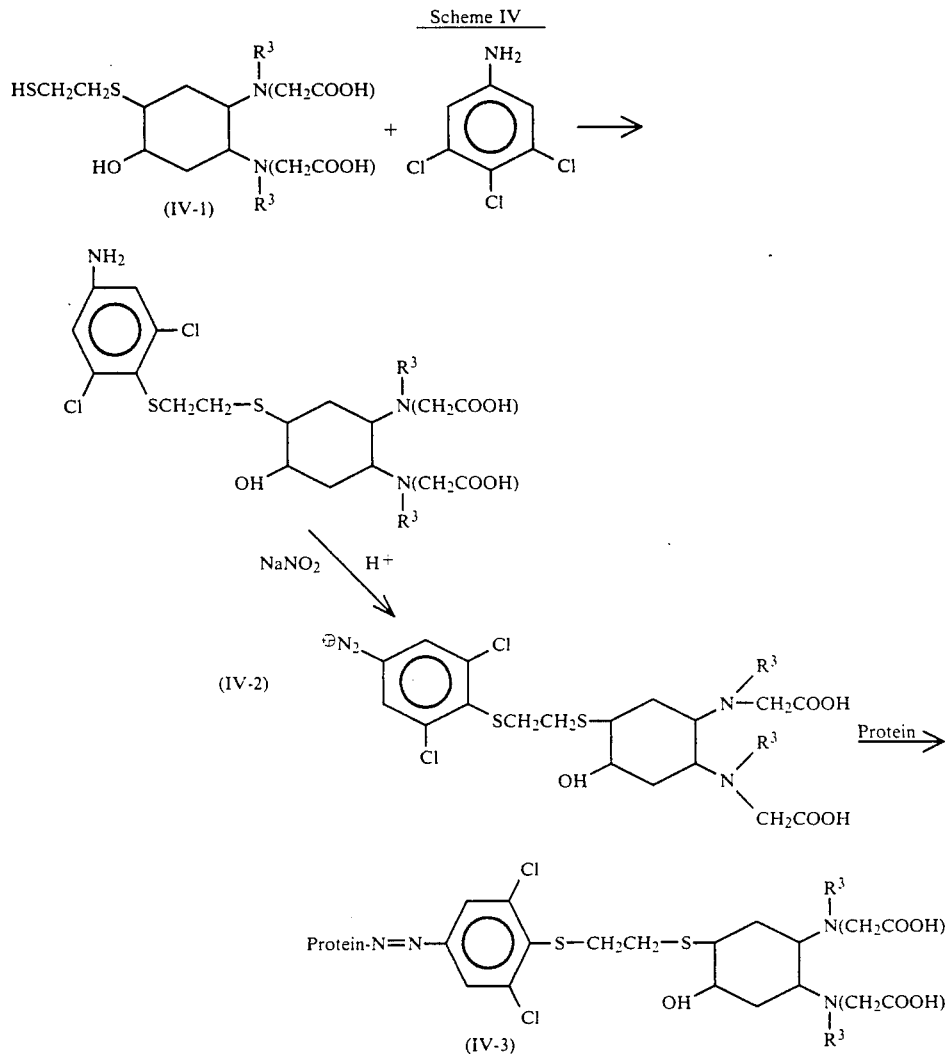

Second, one can attach an A³ moiety containing a reactive group, to a previously prepared X'—R—S—Det$^b$, where X' is a group capable of reacting with the modifiable reactive group on A³, to yield X.

In the third approach, for example, one can previously modify A³ by reacting modifiable reactive groups thereon with a haloacyl group, and then reacting this modified A³ with a modified cyclohexane containing a nucleophilic group such as a thiol or amine (Scheme V).

A³—NH₂

Scheme V

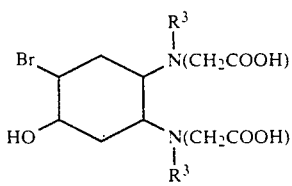

Scheme V

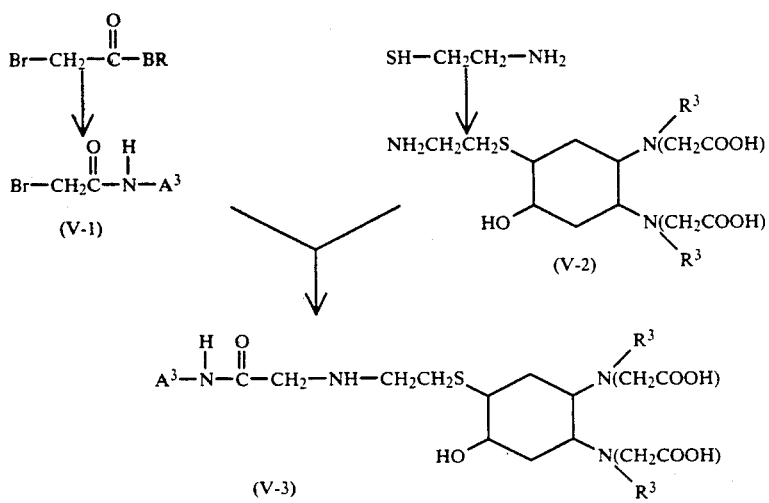

The preparation of haloacyl $A^3$'s as in Scheme V is shown, for example, in the book "Chemical Modification of Proteins", by Means and Feeney, Holden-Day, Inc., 1971, and in Rowley et al, U.S. Pat. No. 4,220,722, both of which are herein incorporated by reference.

The "$A^3$-NH" moiety in Scheme V above can also be modified instead by means of a compound containing a diazo aryl group (such as a 3,4,5 trichlorobenzenediazonium salt) containing a leaving group. Such a compound is known in the tetrafluoroborate form (Korzeniowsky et al, Journal of Organic Chemistry, 1981, 46:2153-2159). Attachment of this compound to a modifiable reactive group $A^3$ modifies the resulting $A^3$ by attaching thereto a displaceable chlorine atom. (Such a scheme would be a modification of Scheme IV, above, obtained by inverting the steps). Generally, the attachment of (other) aryl diazonium functions to biopolymers is known (see Seed, U.S. Pat. No. 4,286,964, and Meares et al, U.S. Pat. No. 4,043,998).

Other possible $A^3$ modifications, especially for biopolymers, useful to prepare the final products of the present invention comprise the reaction of amino groups with diketene to yield acetoacetyl containing $A^3$'s, possibly followed by reduction. (Means and Feeney, supra, page 80-81). The availability of the ketone group of acetoacetyl is useful in reductive amination reactions, where the cyclohexane chelator carries a nucleophilic amine.

Amine-containing biopolymers can be reacted with imido esters in alkaline solution to form imido amides, so-called amidines (Means and Feeney, supra, page 90-91). Reaction occurs at moderately alkaline pH, in aqueous solvent and at room temperature. Appropriately substituted amidines can be prepared which are then capable of reacting with modified cyclohexane chelators.

Sulfonyl halides and substituted sulfonyl halides, such as chlorides and fluorides, are known to react with amino, sulfhydro, imidazole, and phenolic hydroxy groups of proteins (Means and Feeney, supra, page 97). Reaction with aliphatic hydroxy groups is somewhat slower. Appropriately substituted sulfonyl halides can be used to introduce displaceable groups, such as displaceable chlorines, into a biopolymer.

Individual modified mononucleotides can be prepared by applying any of the above-described methods to said mononucleotides.

Attachment of $Det^b$ to polysaccharides can be carried out e.g. by reacting any cis-diol containing polysaccharide with cyanogen biomide and then reacting the resulting water soluble or insoluble activated polysaccharide with an appropriately modified, nucleophilic group containing a cyclohexane chelator a precursor thereof, or biotin. The same scheme can be applied to the preparation of low molecular weight cis-diol containing molecules, such as digoxin, for example.

The attachment of a detectable moiety comprising biotin would generally require modification of the biotin side chain by attachment of a sulfur-containing nucleophile. An example of such a modification is shown below in Scheme VI:

Scheme VI

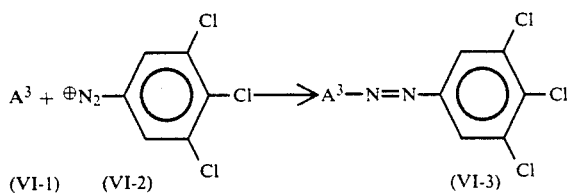

-continued
Scheme VI

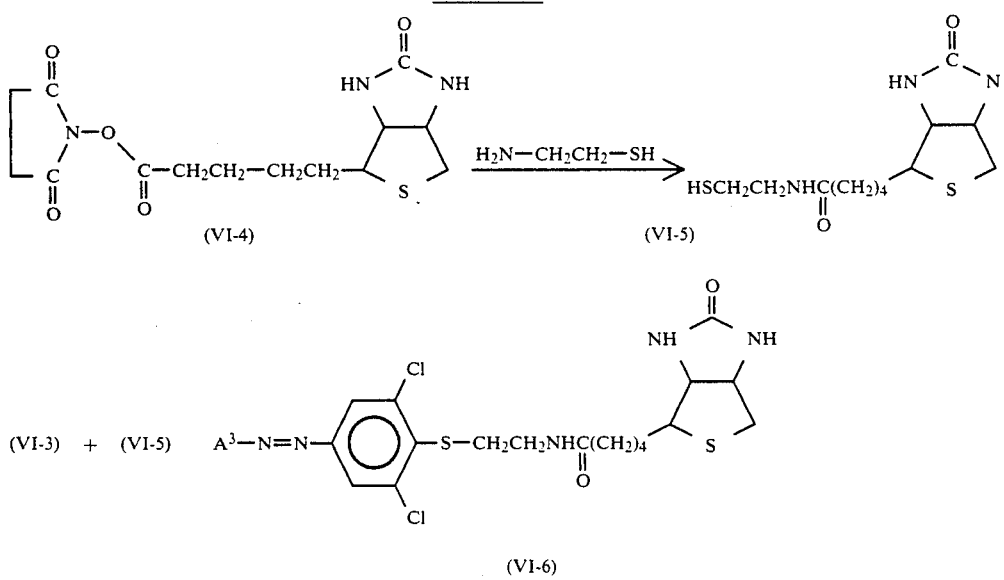

(VI-3) + (VI-5)

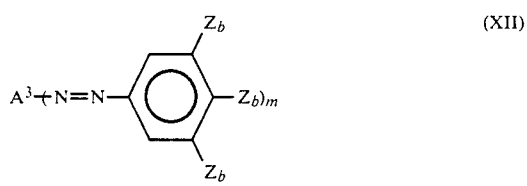

(VI-6)

Scheme VI exemplifies the use of 1-amino, 2-mercapto ethane. The Scheme also exemplifies the use of 3,4,5 trichlorobenzenediazonium salt, but other such coupling agents can be utilized. For example, when $A^3$ is a biopolymer, the same can be modified with a suitable halide, and the mercapto derivative VI-5 can be reacted therewith to yield the final product.

Generally, the reactions with the cyclohexane chelator or derivatives thereof can be carried out with the molecule in the neutralized form (COOH or COONa or COOalkyl form), or in the presence of stoichiometric amounts of other metals such as magnesium. Preparation of the active, detectable cyclohexane moiety containing radiolabelled metal or metal capable of being detected by or imaged by nonradioactive methodologies (NMR, ESR, etc.) can be carried out after the final step in the organic synthesis.

Of particular interest is the preparation of a radiolabelled product prior to the utilization of the agent. A method of preparing a radioactively labelled diagnostic or therapeutic molecule generally comprises contacting a therapeutic or diagnostic agent comprising a molecularly recognizable portion and a chelating portion capable of chelating with a radioactive metal ion, with an ion exchange material having the radioactive metal ion bound thereto and having a binding affinity for the radioactive metal ion less than the binding affinity of the chelating portion for the radioactive metal ion, wherein, prior to the contact, the chelating portion is unchelated or is chelated with a second metal ion having a binding affinity with the chelating portion less than the binding affinity of the radioactive metal ion, whereby a radiolabelled therapeutic or diagnostic agent is produced by the contacting, and then separating the radiolabelled therapeutic or diagnostic agent from the ion exchange material. The so formed radiolabelled material is then immediately used in an in vitro or in vivo diagnostic procedure. Such a method is disclosed in commonly assigned co-pending application U.S. Pat. No. 4,703,440 filed on even date herewith by Y. Stavrianopoulos, for "METHOD OF RADIOACTIVELY LABELLING DIAGNOSTIC AND THERAPEUTIC AGENTS CONTAINING A CHELATING GROUP," herein fully incorporated by reference.

Among other aspects of the invention are various intermediates used in the aforementioned synthetic procedures. Thus, the invention also includes a modified compound of the formula (XII):

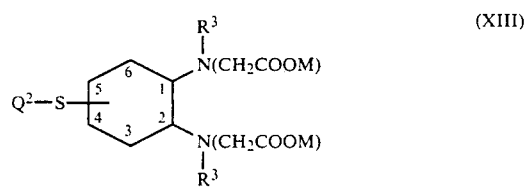

where $A^3$ is as defined above, and contains at least one modifiable reactive group selected from the group consisting of amine and a residue comprising an activated carbon;

$Z_b$ is chlorine, bromine or iodine; and m is an integer from 1 to the total number of modified reactive groups on $A^3$.

This modified $A^3$ is useful in preparing the preferred final detectable products of the invention.

The invention also includes a compound of the formula (XIII):

$$Q^2-S-\underset{R^3}{\underset{|}{\overset{R^3}{\underset{|}{\text{cyclohexane}}}}}\text{(XIII)}$$

(with N(CH$_2$COOM) groups at positions 1 and 2)

or the 4-hydroxy or acyloxy derivative thereof, where M is as defined previously;

—S— is divalent sulfur atom; and $Q^2$— is H; branched or unbranched $C_1$-$C_{10}$ alkyl or aralkyl which carries a group selected from the group consisting of —OH, —SH, —NH$_2$, —CONHNH$_2$, or —C—Lv, where Lv is a displaceable leaving group; or $Q^2$ is

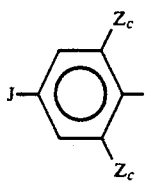

where $Z_c$ is hydrogen, chlorine, bromine or iodine, and J is $-NH_2$ or $-N_2^+CA^-$, where $CA^-$ is a counteranion.

Examples of Lv are $-N_3$, $-Cl$, $-Br$, tosylate, mesylate, and the like. Examples of $CA^-$ are fluoroborate, tetrafluoroborate, tosylate, perchlorate, and the like.

Still other intermediates are modified mononucleotides of the formula XIV:

where $P_z$, BA and $Q^1$ are as defined above.

The modified mononucleotides (XIV) can be integrated into a polynucleotide and then reacted with appropriate SH-group containing cyclohexane chelator or biotin. Alternatively, the modified mononucleotides (XIV) are reacted with a cyclohexane chelator or biotin, and the resulting products are incorporated into a polynucleotide.

Still other intermediates include compounds of the formula XV:

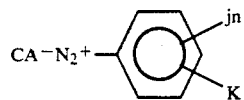

wherein j, n and K are as defined previously, and $CA^-$ is a suitable counteranion.

The preparation of small molecular weight chelator-containing compounds (V):

$$A^1 \cdots Det^a \quad (V)$$

can be carried out by any of the well known methods of linking metal chelating moieties or potential metal chelating moieties to molecules. For example such chelators as EDTA, DTPA or DCTA can be attached to amino or hydroxy groups of $A^1$ with formation of amides or esters. Diazoaryl containing chelators or potential chelators can be attached to activated aromatic groups on $A^1$.

Applications

The uses and applications of the chelator or biotin-containing compounds of the invention are unlimited, and extend to all of those uses to which detectably labelled compounds of this type had been put in the prior art. For example, any compound desired to be detected and analyzed in a sample can be modified according to the techniques of the present invention. Of particular interest are the modification of antibodies for use in immunoassay procedures, such as sandwich immunoassay procedures. Also of interest is the modification of drugs for radioimmunoassay procedures or of proteins associated with or known to be present on microorganism walls or membranes. Detectably labelled proteins prepared in such manner can also be used in competitive immunoassay procedures. Labelled polynucleotides can be used in hybridization assays.

Another use of the detectable compounds, especially biopolymers, of the invention is in imaging, especially with monoclonal antibodies. These can be modified according to the techniques of the invention and allowed to carry a metal onto a given site in a living material, such as an animal body. Detection can then be carried out by radiological techniques. A metal carried to such site can also be chosen to be an emitter, thus producing localized radiotherapy (see, e.g., Denardo, S. et al, in "Nuclear Medicine and Biology," Vol. IV, Pergamon Press, Paris, France, 1982, pp. 182-185.)

Of particular interest is the detection and identification of viral and bacterial DNA sequences.

Polynucleotide products prepared according to this invention can be utilized to diagnose genetic disorders by preparing a polynucleotide complementary to a DNA gene sequence which is associated with a genetic disorder, and detecting the presence of hybridization events. Detectable polynucleotides can also be used in chromosomal karyotyping, which comprises using a series of modified polynucleotides corresponding to a series of defined genetic sequences located on chromosomes, and then detecting hybridization.

Another use includes a method for identifying or locating hormone receptor sites on the surface of cells, which comprises binding a hormone receptor binding compound which is a detectable biopolymer under this invention, and then detecting binding by means of a detection system.

Another use of the metal chelating conjugates of the present invention is in the removal of unnecessary and dangerous accumulations of metal ions from targets specified by a particular biopolymer to which the chelator portion is attached. Generally, the chelatorlabelled molecules of the invention can be used in other detection systems known or later discovered. These uses include chelation with nonradioactive heavy metal ions for use as radioopaque agents, chelation with a metal ion detectable by NMR, chelation with a metal having catalytic properties and capable of catalyizing a chromogenic chemical reaction, and the like.

Biotin bound compounds can be detected by carrying out their incubation with avidin or streptavidin, wherein the avidin or streptavidin is covalently coupled to a detectable label such as an enzyme (e.g., alkaline phosphatase or peroxidase) capable of catalyzing the formation of a chromogenic product. This is the standard, well known enzyme linked immunoassay system (ELISA) and is described in co-pending patent application Ser. No. 392,440 filed on June 23, 1982 to "Modified Nucleotides, Methods of Preparing and Utilizing, and Compositions Containing the Same" by Engelhardt et al, herein fully incorporated by reference.

The present invention also lends itself readily to the preparation of kits. A kit may comprise a carrier being compartmentalized to receive in close confinement therein one or more container means or series of container means such as test tubes, vials, flasks, bottles, syringes, or the like. A first of said container means or series of container means may contain a detectable compound according to the present invention, or the compound present in varying concentrations so as to provide the capability of building a standard interpolation curve. If the chelator bound compound is provided in nonradiolabelled metal form, another container means may contain a desired radiometal and appropriate ion exchange materials to provide for the exchange of "cold" for radioactive metal. Thus, a user can easily label the chelator conjugated compound with a radioactive metal. Alternatively, a second container means or series of container means might contain avidin or streptavidin, such molecules covalently bound to an enzyme for use in an enzyme immunoassay system.

Having now generally described this invention, the same will be better understood by reference to certain specific examples which are included herein for purposes of illustration only and are not intended to be limiting unless so specified.

EXAMPLE 1

Synthesis of 1,2 transdiaminocyclohexene tetraacetic acid

Step 1

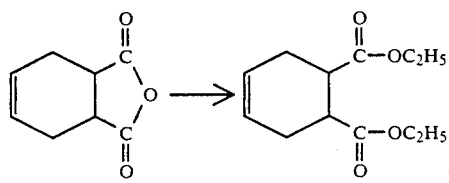

4-Cyclohexene-1,2-dicarboxylic anhydride (154 grams, 1.01 moles) was dissolved in 700 ml of anhydrous 200 grade ethanol. Concentrated sulfuric acid (40 ml) was added, and the reaction mixture was refluxed for three hours. Approximately 350 ml of ethanol was removed by distillation. The distillation also removed water as part of the ethanol-water azeotropic mixture. Approximately 350 ml of absolute 200 grade anhydrous ethanol was added, and then the reaction was allowed to reflux for another 90 minutes. Then, using a rotary evaporator equipped with an air pump (not an aspirator) approximately 400 ml of solvent was removed. One liter of ether was added to the remaining reaction mixture, and the reaction products were dissolved. The reaction mixture was poured into an ice-water mixture (1 liter water and 1 liter ice) and then placed in a separatory funnel. After shaking and allowing the ether and aqueous layers to separate, the aqueous phase was removed and discarded. The ether phase was extracted three times with 100 ml aliquots of cold 5% sodium bicarbonate to remove any H₂SO₄ and monoester. (The pH of the final bicarbonate extract was the same as a fresh 5% bicarbonate solution.) The ether layer was dried over anhydrous Na₂SO₄ with stirring for 90 minutes. The Na₂SO₄ was removed by filtration. The ether was removed from the product 4-cyclohexane-1,2-dicarboxylate ethyl diester on the rotary evaporator and air pump. Gradually, once most of the ether had been removed, the water bath temperature was increased to 90° C. to remove the residual ether quantitatively. A yield of 160 grams of liquid diester was obtained.

Step 2

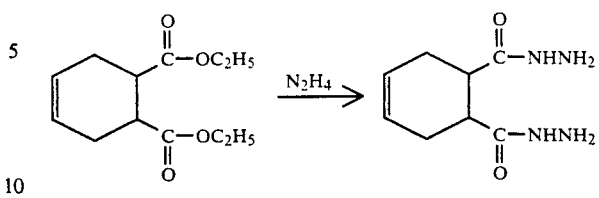

4-Cyclohexene-1,2-dicarboxylate ethyl diester (160 g, 0.707 moles) and 250 ml of commercial grade hydrazine (54% hydrazine=4.22 moles) were placed in a reflux apparatus without stirring. The oil bath was then heated to 130° C. under argon. (The diester and the hydrazine remained in two phases.) Absolute (200 grade) ethanol (less than 100 mls) was added with rapid stirring through the top of the reflux condenser until one phase was obtained. (The milky phase disappeared.) The reaction mixture was refluxed at 130° C. under Argon with stirring (to avoid bumping) for 24 hours. The product 4-cyclohexene 1,2-dihydrazine precipitated as it formed. While the reaction mixture was still warm, it was poured into a 2-liter beaker and allowed to cool. The mixture solidified, and the crude product was filtered on a Buchner Funnel. During filtration, the solid, while still on the Buchner Funnel, was washed with ethanol. The crude hydrazide was recrystallized as follows:

One liter of 85% ethanol (in water) was heated with stirring. A portion (40–50 g) of the crude hydrazide was added. The hydrazide dissolved while the mixture was boiled for 10 minutes. The solution was decanted to remove any insoluble material, and the solution was allowed to cool slowly at room temperature. As the solution cooled, the hydrazide precipitated. It was filtered using a Buchner Funnel and then washed with a small amount of ethanol.

The volume of the filtrate was adjusted to 1 liter with absolute ethanol. The filtrate was then heated with stirring, and another 40–50 g of the crude hydrazide was recrystallized as described above. The procedure was repeated until all of the crude hydrazine had been recrystallized. A total of 120 grams of the hydrazine was obtained.

Step 3

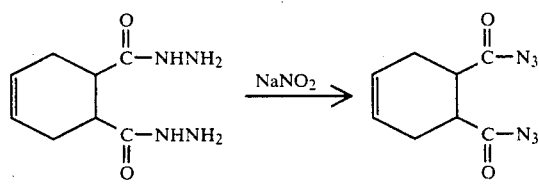

4-Cyclohexene-1,2-dihydrazide (20 g, 0.101 moles) was dissolved in 200 ml of 2N sulfuric acid. Ether (250 ml) was added, and the reaction flask was placed in an ice-salt bath and allowed to cool to −2° to −3° C. Over a 5–10 minute period solid sodium nitrite (13.9 g, 0.202 moles) was added with vigorous stirring. The temperature of the mixture was not allowed to exceed 5° C. Stirring was continued for 10 minutes. The reaction mixture was poured into a cold separatory funnel (the separatory funnel and a one-liter Erlenmeyer flask had been chilled in the freezer), and the phases were allowed to separate. The ether phase was transferred to the cold Erlenmeyer. The aqueous phase was extracted two times with approximately 100–150 ml portions of cold ether as follows. The aqueous phase was stirred with the ether in an ice bath (no salt) for 10 minutes, and then the phases were separated using the cold separatory funnel. The cold ether extracts were combined and then extracted two times with 30 ml portions of cold 5% sodium bicarbonate solution. The ether phase was dried over 60 g of anhydrous sodium sulfate by stirring for 30 minutes at 4. The sodium sulfate was removed by filtration through glass wool. The product 4-cyclohexene-1, 2-diazide (in ether) was not purified or characterized. In order to proceed with the next reaction, the azide was transferred from ether to benzene as follows. An aliquot (approximately ⅓ total ether volume) of the ether solution containing azide was added to approximately 150 ml anhydrous benzene. The ether was evaporated quickly using the rotary evaporator and air pump. The temperature of the water bath was kept below 45° C. during removal of the ether. Additional aliquots of the azide in ether (approximately ⅓ each time) were added until all of the azide had been transferred to the benzene.

Step 4

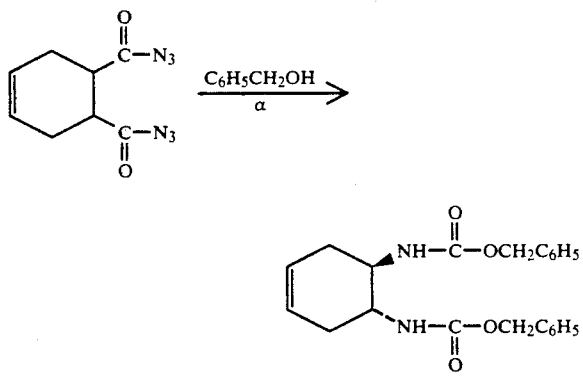

100 ml absolute toluene (100 ml) and benzyl alcohol (30 ml, 0.289 moles) were placed in a flask and heated to 70° C. Aliquots (10 ml) of the 4-cyclohexene,2-dicarboxyl azide in benzene solution (from the previous step) were added slowly (total time for approximately 150 mls benzene solution was approximately 30 minutes) to contain the N₂ evolution, and to prevent the temperature from exceeding 80° C. All of the benzene solution from the previous step was added.

At this point, another 20 g of hydrazide from the prior step was converted to the azide. However, the above procedure was amended as follows. Only 100 ml (not 150) benzene was used per 20 g of hydrazide starting material. The remaining toluene-benzyl alcohol mixture from above was supplemented with 20 ml benzyl alcohol, and then the 100 ml benzene solution was reacted in 10 ml aliquots as described above. This procedure was repeated for a third 20 g batch of hydrazide. The three batches were combined and 10 ml of benzyl alcohol was added (for a total of 0.772 moles per 60 g hydrazide). As much benzene as possible was removed by distillation, and then the remaining reaction mixture was allowed to reflux overnight at a bath temperature of 120° C. During this time, the reaction mixture became reddish-brown. The toluene was removed on the rotary evaporator equipped with a vacuum pump (0.5 mm Hg). Acetic acid (100–200 ml 50% glacial acetic acid in water) was added to the reaction flask, and the mixture was stirred with a glass rod. The desired urethane product (4-cyclohexene-trans-1,2-dibenzylurethane) was insoluble, but the reddish-brown color went into the liquid phase. The urethane product was filtered on a Buchner funnel and washed with cold 50% glacial acetic acid in water. For analysis, the urethane was recrystallized from 50% glacial acetic acid in water. A yield of 60 grams of the urethane was obtained.

Step 5

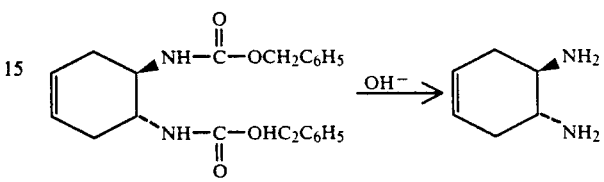

4-Cyclohexene-trans-1,2-dibenzylurethane (60 g) from the previous step was added to 300 ml of 7N sodium hydroxide and refluxed for one hour. Using a very efficient condenser, approximately 70 ml water was removed by distillation to give a final sodium hydroxide concentration of approximately 10N. At this concentration of sodium hydroxide, the sodium carbonate produced during the reaction precipitated. The mixture was allowed to cool, and then the sodium carbonate was removed by filtration on a Buchner Funnel. The sodium carbonate was washed with 100–150 ml n-butyl alcohol. The resulting filtrate had two phases. The filtrate was placed in a separatory funnel and shaken, and the water layer was removed. Then 150 ml water and concentrated hydrochloric acid were added until the pH was 1. The mixture was shaken and the phases were allowed to separate. At this point, most of the product trans-1,2-diamino-4-cyclohexene was in the dihydrochloride form in the aqueous phase. Concentrated hydrochloric acid (50 ml) was added to the organic phase, and more of the product amine dihydrochloride precipitated. The solid was filtered on a Buchner Funnel and then dried in a dessicator over sodium hydroxide pellets to remove the hydrochloric acid. The aqueous phase containing most of the product was evaporated to dryness on the rotary evaporator equipped with a vacuum pump (0.5 mm Hg). The two batches of the product were combined and used in the next step without further purification. It was assumed that there was 100% conversion to the amine.

Step 6

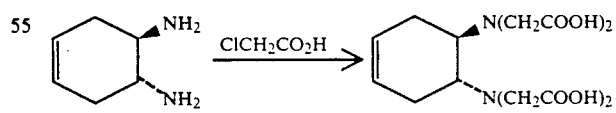

The amine trans-1,2-diamino-4-cylohexene in the hydrochloride form (assumed quantitative conversion from urethane, 0.158 moles) and 75 g chloroacetic acid (0.79 moles) (both solids) were combined in an Erlenmeyer flask equipped with a large stirrer and an ice bath. Cold 7N sodium hydroxide (approximately 113 ml) was added slowly to neutralize the chloroacetic acid. Care was taken to keep the reaction mixture cool (below 20° C). Addition of sodium hydroxide then produced a suspension of the amine. The reaction mixture was gently stirred and heated in a 55° C. oil bath. Using a pH meter to monitor the pH, 7N sodium hydroxide was added to keep the pH between 9 and 10. Once all the amine had dissolved, the oil bath temperature was increased to 90°-95° C. for one hour. During this time, the pH was maintained between 9 and 10 with 7N sodium hydroxide. The reaction mixture was allowed to cool, and then the pH was adjusted to 1.2 with concentrated hydrochloric acid. One liter of acetone was added slowly at room temperature, and the bulk of the side product, sodium chloride, precipitated. The sodium chloride was removed by filtration on a Buchner Funnel. The desired product, trans-1,2-diamino-4cyclohexenetetraacetic acid, remained in the filtrate, which was light red-brown in color. The acetone was removed by a rotary evaporation, using a bath temperature at the end of 80° C. The product remained in aqueous solution and was allowed to cool overnight. A slight precipitate appeared. The pH was readjusted to 1.2 (it was 0.9), and the walls of the flask were scratched to induce crystallization. Further stirring with a magnetic stirrer resulted in further precipitation of the product. The product, trans-1,2-diamino-4-cyclohexenetetraacetic acid (11 g), crystallized from the first crop, and 6 g additional product precipitated slowly over a one month period. The precipitate was collected by filtration, washed with cold water, and dried under vacuum at 100° C. A total of 17 grams of the monounsaturated DCTA product was obtained.

EXAMPLE 2

4-bromo-5-hydroxy-DCTA

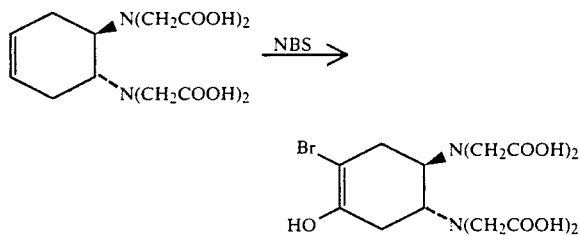

N-bromosuccinimide (NBS) was recrystallized according to the following procedure. One liter of water was placed in a flask equipped with a magnetic stirrer and heated to 75° C. Crude NBS (100 g which had been ground to a fine powder using a mortar and pestle) was added with stirring and then stirred for two minutes. The solution was filtered quickly through a warm Buchner Funnel. (The funnel must be warm; otherwise a precipitate will form during the filtration.) The filtrate was poured quickly into an ice cold beaker to precipitate the NBS while minimizing its decomposition. The NBS was lyophilized overnight to remove traces of water. A total of 80 grams was recovered.

Trans-1,2-diamino-4-cylohexenetetraacetic acid (1 g, (0.0028 moles) free acid was dissolved in 1.5 ml 7N NaOH to give a final pH of approximately 5.2. The solution was cooled to 10° C. and then added to 0.5 g NBS (0.0028 moles) on a glass tube equipped with a magnetic stirrer and an ice bath. The reaction mixture was stirred with the thermometer, and the temperature was kept at 8°-10° C. for 1 hour. The mixture was stirred overnight at 4° C. The reaction was judged to be complete when solid was no longer visible. The product 4-bromo-5-hydroxy-DCTA, in the form of the sodium salt, was precipitated by the addition of 10 volumes of dry methanol. The product was collected by filtration on a Buchner Funnel, washed with a small amount of methanol, and quickly air dried. Exposure to light was minimized to prevent decomposition. The product was placed in an aluminum-foilcovered flask and lyophilized under high vacuum overnight. A total of 1 gram of the sodium salt was obtained. (The stereochemistry around the Br— and OH— bearing carbons has not yet been fully elucidated. For purposes of this invention, however, the stereochemistry is not critical.)

EXAMPLE 3

5-hydroxy-DCTA-4-β-thiopropionic acid hydrazide

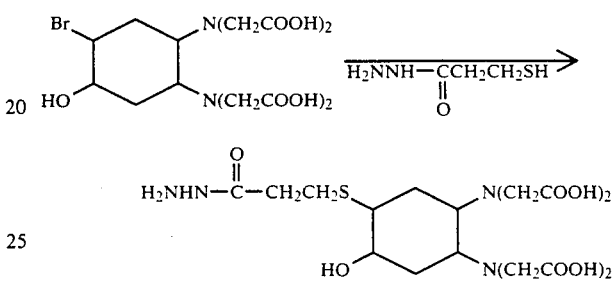

Before this reaction can be performed, the reactant β-mercaptopropionic acid hydrazide must be synthesized, according to the following procedure. β-Mercaptopropionic acid (53 g, 0.5 mole, liquid) was mixed with 0..6 moles NaOH (24 g), 0.2 moles KI (33.2 g), and 0.5 moles crystalline $I_2$ (126.9 g). The bisthiol formed and precipitated at once. It was filtered on a Buchner Funnel, recrystallized from water, and dried for 15 minutes at 95° C. to give 48 g (0.23 moles, 92% yield) of the bisthiol dipropionic acid.

The bisthiol dipropionic acid (48 g, 0.23 moles) was dissolved in 400 ml of absolute ethanol containing 10 ml concentrated sulfuric acid (0.138 moles), and the mixture was refluxed for 2 hours. Ethanol (200 ml) was removed by distillation. Absolute ethanol (an additional 200 ml) was added to the mixture, the mixture was refluxed for another 2 hours, and 200-250 ml ethanol were removed by distillation. Ether (500 ml) was added to the product solution and then the mixture was poured onto ice. Solid sodium bicarbonate (30.7 g, 0.366 moles) was added with stirring to neutralize the solution. The phases were separated in a separatory funnel. The aqueous phase was discarded. The ether phase was washed once with 100 ml cold 5% sodium bicarbonate followed by one wash with 200 ml 0.1M sodium chloride. The ether layer was dried over 50 g anhydrous $Na_2SO_4$ with stirring for 90 minutes. The $Na_2SO_4$ was removed by filtration. The ether was removed from the product [$(CH_3—CH_2—O—CO—CH_2—CH_2S)_2$] on the rotary evaporator equipped with an air pump. Gradually, once most ether had been removed, the water bath temperature was increased to 90° C. to remove the residual ether quantitatively. The crude product was then mixed with 100 ml commercial grade hydrazine (54% hydrazine=1.7 moles) and 100 mls absolute ethanol to convert the ethyl ester to the hydrazide. The mixture was refluxed with stirring overnight under argon to prevent oxidation. The solution became yellowish brown. The ethanol was removed by rotary evaporation. The solid product was triturated with 200 ml absolute ethanol and then collected by filtration on a Buchner Funnel. The product, which was a yellow powder, was recrystallized from 250 ml ethanol to yield 20.3 g bisdithiol hydrazide ($NH_2$—NH—CO—$CH_2$—$CH_2S$—)$_2$ (0.17 moles, 37%). The product was reduced in one step with a 30-fold molar excess of sodium borohydride as follows.

Bis dithiohydrazide (0.75 m moles) was dissolved in 1.0 ml water. Solid sodium borohydride (2.25 moles, 85 mg) was added, and the reaction temperature was maintained at 25° C. with occasional cooling. Formation of the product thiol was monitored at 5 minute intervals as follows. A 5 μl aliquot was dissolved in 200 μl cold water, and the remaining borohydride was destroyed by the addition of 50 μl 1N HCl. Thiol was determined with Cleland's reagent.

When the reaction was complete, the mixture was cooled and 1N HCl was added, dropwise, to destroy the excess borohydride. HCl (1N) was added until gas evolution was no longer observed. The reaction mixture was neutralized to pH 7.8 with 5N NaOH. Indicating paper was used to monitor the pH. At this point, the desired final product, β-mercaptopropionic acid hydraze, was obtained. It was used immediately as follows.

4-Bromo-5-hydroxy-DCTA (441 mg, 1 mmole) and 1 ml 2M potassium carbonate were added to the β-mercaptopropionic acid hydrazide, reacted 2 hrs. at 95° C. under argon and then the reaction mixture was cooled, diluted with water and loaded onto a Dowex 1 column. The unreacted hydrazide did not bind to the column and was monitored in the column break-through with picrylsulfonic acid (production of a red colored solution). The column was washed with 0.1N acetic acid and then the product 5-hydroxy-DCTA-4-thiopropionic acid hydraze was eluted with 0.2N HCl. The hydrazide positive fractions (as monitored by reaction with picrylsulfonic acid) were combined and then neutralized with 5M NaOH. A yield of 0.6 mmoles was obtained.

EXAMPLE 4

4-aminoethylthio-t-hydroxy-DCTA
(5-hydroxy-DCTA-4-β-thioethylamine)

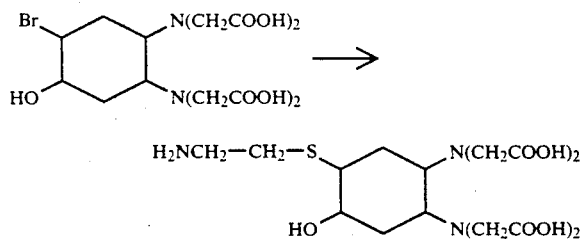

4-Bromo-5-hydroxy-DCTA mg, (882 mg, 2.0 mmol) and 340 mg 2-aminoethanethiolhydrochloride (3.0 mmol) were combined in 1.0 ml 2M potassium carbonate under argon, and then heated for 2 hours at 90° C. The reaction was monitored by following the disappearance of thiol using Cleland's reagent [5,5'-dithiobis-(2-nitrobenzoic acid)]. After approximately 90% of the thiol had disappeared, the reaction mixture was diluted approximately 50-fold with oxygen-free water and then loaded onto a 6 ml Dowex-1 column (acetate form, 0.8 meg/ml resin). The unreacted 2-aminoethanethiol hydrochloride did not bind the column. The column was washed with 0.1N acetic acid. The wash was monitored for the presence of amine using ninhydrin. Some amine bound as salt to the product was washed off as peak and then levels of amine plateaued. At this point, the column was eluted with 0.2M HCL (approximately pH 1). During the elution, part of the product 4-aminoethylthio-5-hydroxy-DCTA precipitated; however, when the pH reached approximately 1, the product dissolved, so care must be taken to elute all of the product.

The eluant was tested for amine using ninhydrin. All amine-positive fractions were combined and lyophilized. A yield of 1.07 g of the product as the amine trihydrochloride was obtained.

EXAMPLE 5

Synthesis of Modified Nucleotide—dUTP allyamine (a) Preparation of mercurated dUTP Deoxyribouridine triphosphate (dUTP; 554 mg) was dissolved in 100 ml of 0.1 M sodium acetate buffer pH 6.0, and mercuric acetate (1.59 gm, 5.0 mmoles) was added. The solution was heated at 50° C. for 4 hours, then cooled on ice. Lithium chloride (392 mg, 9.0 mmoles) was added, and the solution was extracted six times with an equal volume of ethyl acetate to remove excess $HgCl_2$. The efficiency of the extraction process was monitored by estimating the mercuric ion concentration in the organic layer using 4,4'-bis (dimethylamino)-thiobenzophenone (A. N. Christopher, Analyst, 94, 392 (1969)). The extent of nucleotide mercuration, determined spectrophotometrically followed iodination of an aliquot of the aqueous solution as described by Dale et al. (R. M. K. Dale, D. C. Ward, D. C. Livington, and E. Martin, *Nucleic Acid Res.* 2, 915 (1975)), was routinely between 90 and 100%. The nucleotide products in the aqueous layer, which often became cloudy during the ethyl acetate extraction, were precipitated by the addition of three volumes of ice-cold ethanol and collected by centrifugation. The precipitate was washed twice with cold absolute ethanol, once with ethyl ether, and then air dried. These thus-prepared mercurated nucleotides were used for the synthesis of the allylamine-nucleotides without further purification.

(b) dUTP allylamine

1 The mercurated nucleotide (of step a) was dissolved in 0.1M sodium acetate buffer at pH 5.0 and adjusted to a concentration of 20 mM (100 OD/ml at 267 nm). A fresh 2.0M solution of allylamine acetate in aqueous acetic acid was prepared by slowly adding 1.5 ml of allylamine (13.3 mmoles) to 8.5 ml of ice-cold 4M acetic acid. Three ml (6.0 mmoles) of the neutralized allylamine stock was added to 25 ml (0.5 mmole) of nucleotide solution. One nucleotide equivalent of $K_2PdCl_4$ (163 mg, 0.5 mmole) dissolved in 4 ml of water, was then added to initiate the reaction. Upon addition of the palladium salt (Alfa-Venton) the solution gradually turned black with metal (Hg and Pd) deposits appearing on the walls of the reaction vessel. After standing at room temperature for 18-24 hours, the reaction mixture was passed through a 0.45 mm membrane filter (nalgene) to remove most of the remaining metal precipitate. The yellow filtrate was diluted five-fold and applied to a 100 ml column of DEAE-Sephadex TM A-25 (Pharmacia). After washing with one column volume of 0.1M sodium acetate buffer at pH gradient (0.1–0.6M) of either sodium acetate at pH approximately 8-9 or triethylammonium bicarbonate (TEAB) at pH 7.5. The desired product was in the major UV-absorbing portion which eluted between 0.30 and 0.35M salt. Spectral analysis showed that this peak contained several products. Final purification was achieved by reverse phase—HPLC chromatography on columns of Partisil—ODS2, using either 0.5M NH$_4$H$_2$PO$_4$ buffer at pH 3.3 (analytical separations) or 0.5M triethylammonium acetate at pH 4.3 (preparation separations) as eluents. The 5'-triphosphates of 5-(3-aminopropen-1-yl) uridine (the allylamine adduct to uridine) were the last portions to be eluted from the HPLC column, and they were clearly resolved from three as yet uncharacterized contaminants.

EXAMPLE 6 dUTP allylamine labelled with 5-hydroxy-DCTA-4-β-thiopropionic acid hydrazide

5-Hydroxy-DCTA-4 β-thiopropionic acid hydrazide (12 mmoles, 4-fold excess) was dissolved in 0.3 ml water. HCl (50 l, 1N) was added, and the reaction mixture was cooled to 0° C. Cold 0.05 M NaNO$_2$ (0.3 ml; was added to the reaction mixture which was allowed to react at 0° C. for 10 minutes. At this point, the DCTA hydrazide had been converted to the azide (—N$_3$). Potassium carbonate (25 μl 2M) was added to neutralize the reaction mixture and 10 μl 10M magnesium sulfate was added to neutralize the charge. The pH was adjusted to approximately 8 with 15 μl 2M potassium carbonate and then 500 μl of dUTP allylamine (3 mmoles in 0.6M NaCl) and 100 μl cold 5% sodium bicarbonate were added at 0° C. The mixture was allowed to react overnight (approximately 12 hours) at 0° C. The product was separated from unreacted starting materials as follows. The reaction mixture was neutralized to pH 7 with 1N HCl and then loaded onto a 1 ml hydroxylapatite column which had been equilibrated with 0.01M potassium phosphate (equimolar in monobasic and dibasic potassium phosphate, approximate pH 6.8). 0.3 ml fractions were collected. The column was washed with the same buffer (4 ml) until no more absorbance at A$_{260}$ or A$_{255}$ eluted.

The product DCTA-labelled dUTP and any unreacted dUTP allylamine were eluted with 0.3M potassium phosphate buffer (equimolar in monobasic and dibasic potassium phosphate). All fractions with an absorbance of 290 nm were pooled for a total of 0.9 ml. Total A$_{290}$=17.8 OD: E$_{dUPT\ AA290}$=8 nm$^{-1}$, yield of 2.3 μmoles=77%.

The product was transferred to a different buffer according to the following procedure. The product (0.9 mls) was diluted 20-fold with cold water and then loaded onto a 0.5 ml DE-52 cellulose column (chloride form). All A$_{290}$ was absorbed. The column was washed with 0.5 ml (one bed volume) of the 0.05M NaCl. The was eluted with 0.6M NaCl in a volume of 1.0-ml. A$_{290}$ recovered=17.8 OD, for 100% recovery.

A control reaction using dTTP instead of dUTP allylamine was run in parallel and processed similarly. Ten μl of each were diluted with 20 μl glycine 0.05M ammonium acetate in the presence of radioactive nickel and allowed to bind for 15 minutes. Each batch was loaded onto a Dowex 50 (NH$_4$+ form) column. Only the product of the reaction with dUTP allylamine was labelled with the radioactive nickel. At least 84% of the product was the DCTA analogue.

The structure of the chelator-labelled dUTP allylamine product was as follows:

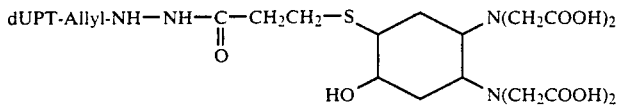

EXAMPLE 7

Protein (Immunoglubulin G) labelled with 5-hydroxy-DCTA

One equivalent DCTA-hydrazide (in water) was treated with a 10-fold excess of 1N HCl and cooled to 0° C. One equivalent of cold 0.05M NaNO$_2$ solution in a precooled pipette was added to the reaction mixture at 0° C. The mixture was allowed to react at 0° C. for 10-15 minutes. The reaction mixture was neutralized (to approximately pH 8.5) with cold 5% sodium bicarbonate. This also resulted in high salt molarity. The Immunoglobulin G protein was added and incubated overnight at 0° C. The excess activated DCTA was retained by a G-50 column, and the protein came through at the void volume.

EXAMPLE 8

DCTA-SH

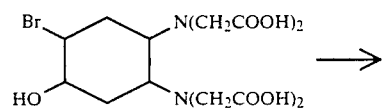

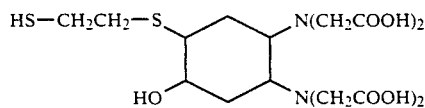

One millimole of DCTA-bromide was added to 5 ml of 50% DMF containing 0.2 ml of 1,2-dithioethylene and 0.5 ml of triethylamine. The mixture was incubated under argon for 2 hours at 60°–70° C. After reaction the mixture was diluted with oxygen-free H$_2$O to 50 ml, the pH was adjusted to 4.0–4.5 with glacial acetic acid and the excess HS—CH$_2$—CH$_2$—SH was extracted three times with 15 ml benzene by stirring (not shaking). The water phase was then loaded onto a Dowex AG-1 column, umn, 9 ml bed volume. The column was washed with 50 ml of 0.1M acetic acid solution until the flow-through was thiol free. The DCTA-SH was then eluted with 0.25 M HCl. The thiol containing fractions were combined, evaporated to dryness under reduced pressure at 40° C. and the free acid (300 mg) was stored at −20° C. under argon.

EXAMPLE 9

Activation of DNA with 3,4,5-Trichloroaniline 100 mg of 3,4,5-trichloroaniline was dissolved in 2.5 ml of 0.5M HCl in 50% DMSO and cooled on ice, under vigorous stirring, an equimolar amount of NaNO$_2$ from a cold 1M solution was added, as rapidly as possible, and then stirring was continued for 10 minutes. 1 mg of 3H or fd DNA in 300 ml of water were mixed with 300 μl 2M cacodylate buffer pH 6.6 and 600 μl DMSO. (By addition of DMSO the pH of the solution rises to 8.3). 20 μl of the freshly prepared diazonium solution were added thereto and the mixture was incubated for two hours at room temperature. The slight precipitate which appeared during the incubation was removed by centrifugation. The solution was then made 0.4M with ammonium acetate and the DNA was precipitated with ethanol.

EXAMPLE 10

Reaction of Trichloroaniline-activated DNA with thiols. Example of Reaction with DCTA-SH fd DNA activated with 3,4,5-Trichloroaniline (Example 9) was dissolved in 0.1M sodium hydroxide with an equal amount of 0.1M $K_2HPO_4$. This solution was treated with an equal volume of 0.1M DCTA-SH (Example 8) and incubated under argon at 65° C. for 2 hours. The precipitated disulfides were removed by centrifugation and the DNA was purified by G50 chromatography and stored at −20° C. Using radioactive Ni to estimate the level of derivatized DNA, it was determined that 60% of guanines had been labelled.

EXAMPLE 11

Biotin-SH

Three millimoles of Biotin-NHS ester were dissolved in 25 ml of anhydrous DMF and mixed with a 1M solution of cysteamine hydrochloride in 12 ml of 0.5M sodium bicarbonate and the mixture was incubated at room temperature overnight. During the incubation, a heavy precipitate appeared. The liquid was removed under reduced pressure at 45° C. and the residue was suspended in 50 ml absolute ethanol, 1 g of $NaBH_4$ was added and the suspension was stirred for one hour at 75° C. The ethanol was removed, cold 1M HCl was added to bring the pH to 4.5, and the water was removed under reduced pressure at 35° C. (All these operations were performed under an argon atmosphere to prevent oxidation of the thiol.) The solid residue was powdered and triturated with 4 ml of cold deareated 0.01M acetic acid. This procedure was repeated twice and the residue was lyophilized. TLC chromatography showed that the main biotin spot contained thiol; two minor spots were thiol negative. In all reactions, the amount of biotin used was based on the thiol content. It is possible to use Biotin-SH in the reaction with trichloroaniline-activated DNA, in analogy to Example 10.

EXAMPLE 12

Labelling of the 3,4,5-trichloroaniline DNA with DCTA-SH 0.5 mg of the activated DNA (Example 9) in 0.2 ml of water were mixed with 2.0 ml of 0.5M triethylammonium acetate in 90% DMF. 50 mg of DCTA-SH (Example 8) in the triethylammonium form were added. The mixture was stirred in the dark for 4 hours at 50° C. The DMF was removed under reduced pressure at 45° C. and the DNA was desalted by G-50 filtration. The degree of labelling was then determined by the use of radioactive Ni-63. On the average every 5.3 bases were labelled, by calculation.

EXAMPLE 13

4-Aminothiophenyl DCTA and 3-Aminothiophenyl DCTA

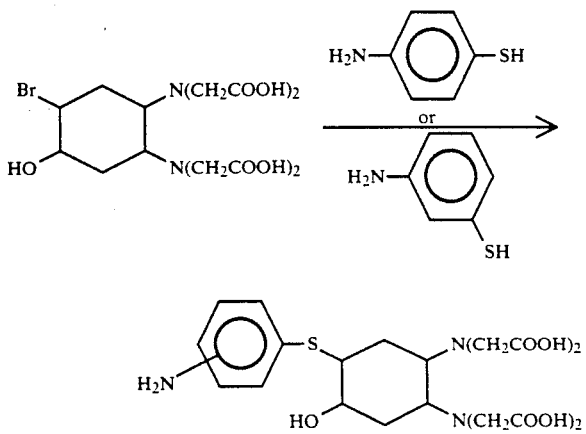

4-Amino: 13-1
3-Amino: 13-2

882 mg of 4-bromo-5-hydroxy-DCTA (2.0 μmole) and 376 mg of 4-aminothiophenol, or 320 μl of 3-aminothiophenol, were dissolved in 2 ml potassium carbonate (1M), and the mixture was stirred for 2 hours at 90° C. under argon. The mixture was diluted with 50 μl oxygen-free $H_2O$ and loaded to a 10 ml Dowex column. The column was washed with 0.1M acetic acid until the flow through was thiol free, and the product was eluted with 0.2 HCl. All thiol containing fractions were combined, and the HCl was neutralized with KOH. The solution was stored at −40° C. The yield determined by the thiol content was 92.7% (13-1) and 86.3% (13-2) respectively.

EXAMPLE 14

Labelling of BSA with 4-aminothiophenyl DCTA

When labelling with 4-aminothiophenyl DCTA (Example 13-1), the stock 4-amino solution was 0.1M. 100 μl of the 4-aminothiophenyl DCTA solution plus 25 μl 1M HCl plus 100 μl of 0.1M $NaNO_2$ were mixed and incubated for 30 min. at 0° C. 50 μl of 1M $K_2HPO_4$ were added to bring the pH to 6.7 and a 50 μl aliquot was mixed with 1 ml of BSA (7.0 mg/ml) in 0.1M. $NABO_3$. The mixture was incubated for one hour at 4° C. The diazonium salt was very labile. After 1 hour at 4° C., no coupling with β-naphthol was observed; the ratio of labelling was 1.7.

The 3-aminothiophenyl DCTA was not used, but due to its high stability it will be a better reagent.

The BSA used here was previously heated for 15 minutes at 95° C. in pH 3.5 to inactivate nuclease.

EXAMPLE 15

Labelling of BSA with DCTA Hydrazide

200 μl of hydrazide solution (6.7 umoles) plus 50 μl 1M HCl were cooled at 0° C. 7 μl of 1M $NaNO_2$ were added and incubated for 15 minutes at 0° C. 30 μl of ice-cold 2M $Na_3CO_3$ were added to the solution to bring the pH to ca. 8.5–9.0. To 1 ml solution of BSA in 0.1M $NABO_3$ (7.0 mg/ml) were added 125 μl of the azide solution and the mixture was incubated overnight at 4° C. The excess of azide was removed by G50 filtration. The BSA filtrate was diluted to 0.5 mg/ml and a 100 μl aliquot was labelled with Ni. Total counts were 86,728 (6.9 l moles). Assuming a MW of 68000 for BSA, the 0.5 mg are 7.3 μmoles (0.72 μmoles in the 100 ml aliquot corresponds to 9.4 DCTA molecules/molecule of BSA).

EXAMPLE 16

λ DNA Hybridization Using a Radio Cobalt-Containing DNA Probe

A. Preparation of DNA Carrying Terminal Poly(allylamine) dUTP 3.2 OD/260, 200 μg λDNA in 200 μl (0.01 buffer Tris-HCl pH 7.4, 0.001M EDTA) were mixed with 80 μl DNAse (diluted 1/5000 with 1 μg/μl BSA; 0.005M $MgCl_2$). The mixture was incubated for 5 min. at 37° C., mixed with 50 μl of 0.1M EDTA and heated for 15 min. at 65° C. to inactivate the enzyme. The incubation mixture was loaded onto a 0.5 ml DEAE column equilibrated in 0.2M KCl, and the column was washed with 5 ml 0.2M KCl. The DNA was eluted with 0.5M KOH. The 260 nm absorbing fractions were combined and neutralized with acetic acid.

The incubation mixture contained in 3.0 ml: 0.2M cacodylate buffer pH 7.3; 0.1M potassium acetate 1 mM dUTP-0.3 mM allyl-amino dUTP; 1 mM $CaCl_2$; 1 mM β-mercaptoethanol; digested DNA and 400 units of terminal tranferase. Incubation proceeded overnight at 37° C. 51.8% of the nucleotide triphosphates were terminally incorporated to the DNA fragments. The mixture was loaded onto a 0.5 ml DEAE column, washed with 10 ml 0.2M KCl and the product was eluted with 1.5M LiCl 9.3 OD/260; 3.2 OD of input=6.1 OD/260=244 μg polymer.

B. Radio Labelling of the Allylamino groups 1 ml hydrazide-DCTA (Example 3) (16.4 mmoles) plus 200 μl 1M HCl were cooled at 0° C. 50 μl of cold 0.35 M $NaNO_2$ were added under stirring and the mixture was incubated for 15 minutes at 0° C. 100 μl of cold 2M $K_2CO_3$ were added to neutralize the acid, followed by the addition of 200 μl 0.5M borate buffer pH 9.2. To this mixture, the "cold" DNA solution (1 ml) was added and incubated overnight at 0° C. The mixture was then loaded on a 0.5 ml DEAE column (equilibrated in 0.2M KCl). The column was washed with 10 ml 0.2M KCl, and the product was eluted with 1.5M LiCl. Half of the OD/260 was eluted with this salt. The rest was eluted with 1.5M LiCl in 0.2M acetic acid. Radioactive $CoCl_2$ was then added in aliquots.
Fr I: 8,800,000 cpm/μg.
Fr II: 92,600,000 cpm/μg Fr I was then hybridized with DNA, as follows.

C. Hybridization

C.1 Southern gels

DNA was restricted with Hind III, chromatographed and transferred by the Southern blot technique to appropriate filters. As control were used restricted M13 phage. Cobalt-labelled DNA (Experiment 16.B, 2 μg), and carrier DNA (1 mg) were dissolved in 5 ml of hybridization solution. The control and test samples were incubated with this solution at 42° C. overnight, then washed 3 times in buffer with 0.1% SDS at 55° C., air dried, and counted in standard toluene cocktail.

Results (1) M13 control: 7475 cpm
(2a) λ test (a): 25,724 cpm
(2b) λ test (b): 29,412 cpm The results indicate that, although background counts are high, hybridization using the cobalt labelled probe yielded about 3.5-4 time higher counts.

C.2 Spot Hybridization

Spot hybridizations were carried out under overnight conditions as described for C.1 above. Using the Co-labelled DNA probe it was possible to detect 125 pg of λ DNA.

EXAMPLE 17

Preparation of Radio-Nickel Labelled Anti HCG Antibody 0.4 $OD/_{280}$ of anti human chorionic gonadotropin antibody + 0.22 μmols of hydrazide DCTA (Example 3) in 250 μl of 0.1M borate buffer were incubated overnight at 0° C. The excess of DCTA hydrazide was removed by G50 filtration.

Filtrate $OD/_{280}$=0.376
$OD/_{280}$=0.216

An aliquot (100 μl) containing the derivatized antibody was mixed with 10 μmols Ni of specific activity 629,262 cpm/μmol. Counts bound to the protein: 297,350 cpm=0.472 μmoles. (Assuming 1.4 $OD/_{280}$ for 1 mg antibody and a molecular weight of 150,000.) The 100 l aliquot contained 0.0376 $OD/_{280}$ which is equal to 26.4 μg=0.175 μmoles of antibody. 0.175 μmoles of antibody contained 0.472 μmoles Ni. Thus, 1 mole antibody contained 0.472/0.176=2.60 moles Ni.

EXAMPLE 18

Recommended Procedure for DCTA-Labelling of Substances with a Free Alcohol Group, which are Soluble in Inert Solvents.

Dowex $1-X2^R$ contains quaternary amino groups. These groups bind the carboxy groups of DCTA-hydrazide very strongly to form the following salt (I):

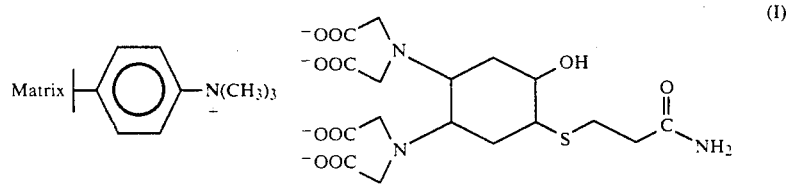

Salt (I) is stable in 0.03M HCl and is displaced at higher (0.1M) HCl concentrations. It is reacted with $NaNO_2$ in 0.03M HCl to form azide (II):

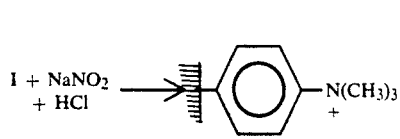 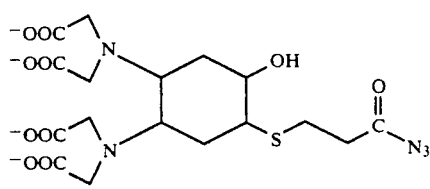

By heating salt (II) in benzene the azide rearranges to form isocyanate (III):

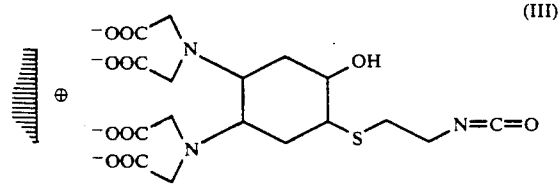

The isocyanate group of (III) then reacts with alcohols at 80°-130° C. to form urethane (IV):

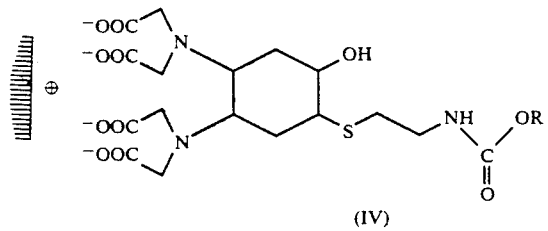

These urethanes are stable substances at physiological pH, and hydrolize to form amines only with conc. acids or conc. alkali. The fixing of the DCTA to Dowex prevents, to a large extent, its —OH group from reacting with the isocyanate group of another molecule, and makes it possible to work in benzene or toluene or other inert solvents where the DCTA azide is insoluble.

After formation of the urethane (IV), the same is eluted from the Dowex with cold LiCl in 50% ethanol. In the cold and at neutral pH no transesterification occurs.

EXAMPLE 19

Labelling of Ceramide

Ceramide is a diglyceride with two free alcohol groups.

10 mmoles of DCTA-hydrazide ((I) from Example 18) were added slowly to a suspension of Dowex AG-1-X2 in 50 ml H$_2$O under stirring. The stirring was continued for 15 minutes and the resin was washed on a Buchner funnel with 500 ml cold water. The resin was then suspended in 100 ml of cold 0.03M HCl, and the suspension was placed in an ice bath. 10 mmoles of solid NaNO$_2$ were added under stirring in a period of 30 minutes, and the temperature was kept below 5° C. After the last NaNO$_2$ addition the suspension was stirred for 15 minutes at the same termperature. The resin was subsequently filtered through a cold Buchner funnel and washed with 100 ml cold (−20° C.) ethanol. It was finally suspended in 100 ml of cold (−20° C.) ethanol and stirred for 30 minutes in an ice-salt bath at −20° C. The ethanol was removed by suction and the remaining traces of ethanol were removed at high vacuum. The dry resin was aliquoted under anhydrous conditions and stored in sealed ampoules at −70° C. without any loss of activity for at least 8 months.

To label the ceramide, 0.5 g of the azide resin were suspended in 15 ml absolute benzene, 600 μmoles of ceramide were added and the suspension was heated for 30 minutes at 75° C. Subsequently, the benzene was removed in a vacuum, 15 ml absolute toluene were added, and the suspension was stirred at 120° C. overnight under anhydrous conditions.

The resin was filtered, washed with ethanol to remove the traces of toluene, and unreacted ceramide was then removed with 3 bed volumes of 50% ethanol in H$_2$O. The product was eluted with 0.6M LiCl in 50% ethanol/H$_2$O. The fractions with DCTA activity were combined, and the ceramide content was determined iodometrically. It was found to be 63.8% of the input.

EXAMPLE 20

A. General DCTA Labelling of Substances with a Cis-Diol Group.

The diol is activated with cyanogen bromide in K$_2$CO$_3$ solution, the excess of cyanogen bromide is inactivated wtih triethanolamine, and the activated diol is reacted with DCTA amine. If the substance is not soluble in water, as is the case of digitoxin, the activation is performed in diglyme/water.

B. Labelling of Digitoxin 65.4 μmoles of $^3$H-digitoxin (1000 cpm/mg) were dissolved in 40 ml of diglyme and cooled to 4° C. An equal volume of 0.1M cold K$_2$CO$_3$ was added and 300 mg of cyanogen bromide, in 2 ml of acetonitrile, were added at once, under stirring and cooling. The mixture was kept for 15 minutes at 4° C. and the excess of cyanogen bromide was inactivated with 5 ml of 2M triethanol amine hydrochloride (pH 1.2), resulting in a pH of 8.5–9.0. 200 μmoles of DCTA-amine, dissolved in 2 ml H$_2$O were added, and the mixture was incubated overnight at 4° C. and subsequently loaded onto a Dowex AG-1-X2 column. The column was washed with 50% ethanol until no counts were contained in the flow through, and the conjugate was eluted with 0.6M LiCl by 50% ethanol. All radioactive fractions were combined. Recovery of the radioactivity, which implies conjugated digitoxin, was 57.6%.

EXAMPLE 21

Labelling of 4-Amino-1-Naphthol Phosphate with DCTA

The procedure developed to label 4-amino-1naphthol phosphate with DCTA applies to all substances having a primary amino group.

A solution of 500 μmoles of 5-hydroxy-DCTA-4-B-thiopropionic acid hydrazide dissolved in 20 ml of 0.2M HCl was cooled to 0° C., and 500 μmoles of solid NaNO₂ were added in a period of 10 minutes so that the temperature remained below 5° C. 15 minutes after the last NaNO₂ addition, the pH was brought to 8.5 with cold Na₂CO₃ and 450 μmoles of 4-amino-1-naphtol phosphate dissolved in 5 ml 1M NaHCO₃ were added. The mixture was incubated overnight at 4° C., diluted with 100 ml of H₂O and loaded onto a Dowex 1-X2 column in the acetate form.

The column was washed with 3 bed volumes 0.1M acetic acid, and the product was eluted with 0.6M LiCl in H₂O. The DCTA-containing fractions were combined, and the product was precipated with 3 bed volumes of ethanol at −20° C. overnight.

Yield: 86.4% of product:

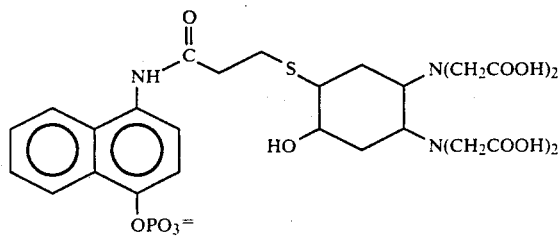

The product is a substrate for alkaline phosphatase. By coupling the formed phenol with a diazonium salt a precipitate appears wich can be labelled with a radioactive metal. This constitutes a very sensitive assay for alkaline phosphatase.

Having now full described this invention, it will be appreciated by those of ordinary skill in the art that the same can be performed within a wide and equivalent range of structures, procedures and uses without affecting the spirit or scope or any aspect of the invention or any embodiment thereof.

What is claimed as new and desired to be secured by Letters Patent of the United States:

1. A detectable molecule of the formula $$A^3-(-X-R^1-E-Det^b)m$$

where $A^3$ is an oligo- or polynucleotide having at least one modifiable reactive group which is attached to the 6 position of the base, when the base selected is adenine, to the 4 position of the base, when the base selected is cytosine, or to the 2 position of the base, when the base selected is guanine, which reactive group consists of amino, hydroxy, cis OH, halide, aryl, imidazoly, carbonyl, carboxyl, thio or a residue comprising an activated carbon;

—X— is selected from the group consisting of: —NH—CO—, —NH—C(NH)—, —N=N—, —NH—SO₂—, —OSO₂—, —NH—N=N—, —NH—CH₂—, —CH₂—NH—, —O—CO—, —NH—CO—CH₂—S—, —NH—CO—CH₂—NH—, —O—CO—CH₂—, —S—CH₂—, —O—CO—NH—

—R¹— is

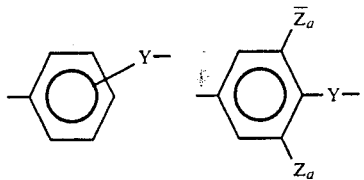

a C₁-C₁₀ branched or unbranched alkyl or aralkyl which may be substituted by —OH;

—Y— is a direct bond to —E—, or —Y— is —E—R²— wherein —R²— is a C₁-C₁₀ branched or unbranched alkyl;

$Z_a$ is chlorine, bromine or iodine;

—E— is O, NH or an acyclic divalent sulfur atom;

$Det^b$ is a chemical moiety capable of being detected, comprising biotin or a substituted metal chelator or a compound cable of yielding a metal chelator; and m is an integer from 1 to the total number of modified reactive groups on said oligo- or polynucleotide.

2. A detectable molecule of the formula $$A^3-(-X-R^1-E-Det^b)m$$

where $A^3$ is an oligo- or polynucleotide having at least one modifiable reactive group which is attached to the 5 position of the base, when the base selected is pyrimidine, or to the 7 position of the base, when the base selected is 7-deazapurine, which reactive group consists of amino, hydroxy, cis OH, halide, aryl, imidazoyl, carbonyl, carboxyl, thiol or a residue comprising an activated carbon;

—X— is selected from the group consisting of: —NH—CO—, —NH—C(NH)—, —N=N—, —NH—SO₂—, —OSO₂—, —NH—N=N—, —NH—CH₂—, —CH₂—NH—, —O—CO—, —NH—CO—CH₂S—, —NH—CO—CH₂—NH—, —O—CO—CH₂—, —S—CH₂—, —O—CO—NH—

—R¹— is

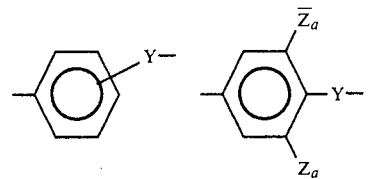

a C₁-C₁₀ branched or unbranched alkyl or aralkyl which may be substituted by —OH;

—Y— is a direct bond to —E—, or —Y— is —E—R²— where —R²— is a C₁-C₁₀ branched or unbranched alkyl;

$Z_a$ is chlorine, bromine or iodine;

—E— is O, NH or an acyclic divalent sulfur atom;

$Det^b$ is a chemical moiety capable of being detected, comprising biotin or a substituted metal chelator or a compound capable of yielding a metal chelator; and m is an integer from 1 to the total number of modified reactive groups on said oligo- or polynucleotide.

* * * * *